United States Patent
Hoffman

(10) Patent No.: US 7,131,973 B2
(45) Date of Patent: Nov. 7, 2006

(54) BONE ANCHOR IMPLANTATION DEVICE

(75) Inventor: Keith Hoffman, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 277 days.

(21) Appl. No.: 10/147,533

(22) Filed: May 16, 2002

(65) Prior Publication Data
US 2003/0216743 A1 Nov. 20, 2003

(51) Int. Cl.
A61B 17/56 (2006.01)
(52) U.S. Cl. .................. 606/72; 606/104; 606/213
(58) Field of Classification Search .............. 606/99, 606/104, 139, 142, 143, 151, 213, 219, 72
See application file for complete search history.

(56) References Cited

U.S. PATENT DOCUMENTS

| | | |
|---|---|---|
| 1,030,530 A | 6/1912 | Palmer |
| 1,066,025 A | 7/1913 | Lieberknecht |
| 1,179,910 A | 4/1916 | Greenfield |
| 1,417,669 A | 5/1922 | Langworthy |
| 2,200,120 A | 5/1940 | Nauth |
| 2,454,680 A | 11/1948 | Stephens |
| 2,635,238 A | 4/1953 | Garland |
| 2,655,921 A | 10/1953 | Haboush |
| 2,666,430 A | 1/1954 | Gispert |
| 3,003,155 A | 10/1961 | Mielzynski et al. |
| 3,388,847 A | 6/1968 | Kasulin et al. |
| 3,551,987 A | 1/1971 | Wilkinson |
| 3,580,313 A | 5/1971 | McKnight |
| 3,593,903 A | 7/1971 | Astafiev et al. |
| 3,596,656 A | 8/1971 | Kaute |
| 3,744,495 A | 7/1973 | Johnson |
| 3,892,232 A | 7/1975 | Neufeld |
| 3,948,477 A * | 4/1976 | Lample .................. 251/8 |
| 3,974,833 A * | 8/1976 | Durden, III .............. 604/20 |
| 4,159,716 A | 7/1979 | Borchers |
| 4,371,124 A | 2/1983 | Gifford et al. |
| 4,414,967 A | 11/1983 | Shapiro |
| 4,415,111 A | 11/1983 | McHarrie et al. |
| 4,421,112 A | 12/1983 | Mains et al. |
| 4,422,567 A | 12/1983 | Haynes |
| 4,438,769 A | 3/1984 | Pratt et al. |
| 4,527,726 A | 7/1985 | Assell et al. |
| 4,535,768 A | 8/1985 | Hourahane et al. |
| 4,537,185 A | 8/1985 | Stednitz |
| 4,545,374 A | 10/1985 | Jacobson |
| 4,569,469 A | 2/1986 | Mongeon et al. |

(Continued)

FOREIGN PATENT DOCUMENTS

EP 0 153 831 A3 9/1985

(Continued)

OTHER PUBLICATIONS

Benderev et al., Anchor Fixation And Other Modifications Of Endoscopic Bladder Neck Suspension, Urology 40: 409-418 (1992).

(Continued)

Primary Examiner—David O. Reip
(74) Attorney, Agent, or Firm—Fish & Neave IP Group, Ropes & Gray LLP

(57) ABSTRACT

Bone anchor implantation devices and methods for their use are disclosed. The bone anchor implantation devices have an ergonometric and/or rotatable handle. The bone anchor implantation devices and methods find particular application for implanting a bone anchor for maintaining or improving urinary continence by suspending or stabilizing the bladder neck.

2 Claims, 18 Drawing Sheets

U.S. PATENT DOCUMENTS

| | | | |
|---|---|---|---|
| 4,576,167 A | 3/1986 | Noiles | |
| 4,606,343 A | 8/1986 | Conta et al. | |
| 4,632,100 A | 12/1986 | Somers et al. | |
| 4,635,634 A | 1/1987 | Santos | |
| 4,664,305 A | 5/1987 | Blake, III et al. | |
| 4,738,255 A | 4/1988 | Goble et al. | |
| 4,739,751 A | 4/1988 | Sapega et al. | |
| 4,741,330 A | 5/1988 | Hayhurst | |
| 4,744,353 A | 5/1988 | McFarland | |
| 4,750,492 A | 6/1988 | Jacobs | |
| 4,784,126 A | 11/1988 | Hourahane | |
| 4,784,137 A | 11/1988 | Kulik et al. | |
| 4,784,138 A | 11/1988 | Sinnett | |
| 4,838,282 A * | 6/1989 | Strasser et al. | 600/567 |
| 4,870,957 A | 10/1989 | Goble et al. | |
| 4,872,451 A | 10/1989 | Moore et al. | |
| 4,873,977 A | 10/1989 | Avant et al. | |
| 4,883,048 A | 11/1989 | Purnell et al. | |
| 4,889,119 A | 12/1989 | Jamiolkowski et al. | |
| 4,898,156 A | 2/1990 | Gatturna et al. | |
| 4,899,743 A | 2/1990 | Nicholson et al. | |
| 4,926,722 A | 5/1990 | Sorensen et al. | |
| 4,940,467 A | 7/1990 | Tronzo | |
| 4,946,468 A | 8/1990 | Li | |
| 4,957,498 A | 9/1990 | Caspari et al. | |
| 4,960,420 A | 10/1990 | Goble et al. | |
| 4,968,315 A | 11/1990 | Gatturna | |
| 4,978,351 A | 12/1990 | Rozas | |
| 4,997,433 A | 3/1991 | Goble et al. | |
| 4,997,434 A | 3/1991 | Seedhom et al. | |
| 4,997,436 A | 3/1991 | Oberlander | |
| 5,002,550 A | 3/1991 | Li | |
| 5,013,316 A | 5/1991 | Goble et al. | |
| 5,030,219 A | 7/1991 | Matsen, III et al. | |
| 5,040,715 A | 8/1991 | Green et al. | |
| 5,046,513 A | 9/1991 | Gatturna et al. | |
| 5,052,607 A | 10/1991 | Dutton | |
| 5,057,112 A | 10/1991 | Sherman et al. | |
| 5,061,181 A | 10/1991 | Niznick | |
| 5,078,730 A | 1/1992 | Li et al. | |
| 5,088,323 A | 2/1992 | Johnson et al. | |
| 5,100,417 A | 3/1992 | Cerier et al. | |
| 5,102,421 A | 4/1992 | Anspach | |
| 5,108,397 A | 4/1992 | White | |
| 5,112,337 A | 5/1992 | Paulos et al. | |
| 5,116,338 A | 5/1992 | Poggie et al. | |
| 5,125,553 A | 6/1992 | Oddsen et al. | |
| 5,129,902 A | 7/1992 | Goble et al. | |
| 5,141,520 A | 8/1992 | Goble et al. | |
| 5,152,790 A | 10/1992 | Rosenberg | |
| 5,156,315 A | 10/1992 | Green et al. | |
| 5,180,388 A | 1/1993 | DiCarlo | |
| 5,188,630 A * | 2/1993 | Christoudias | 606/1 |
| 5,192,303 A | 3/1993 | Gatturna et al. | |
| 5,203,784 A | 4/1993 | Ross et al. | |
| 5,203,787 A | 4/1993 | Noblitt et al. | |
| 5,207,679 A | 5/1993 | Li | |
| 5,217,462 A | 6/1993 | Asnis et al. | |
| 5,217,486 A | 6/1993 | Rice et al. | |
| 5,224,946 A | 7/1993 | Hayhurst et al. | |
| 5,236,445 A | 8/1993 | Hayhurst et al. | |
| 5,242,457 A | 9/1993 | Akopov et al. | |
| 5,258,016 A | 11/1993 | DiPoto et al. | |
| 5,268,001 A | 12/1993 | Nicholson et al. | |
| 5,304,147 A | 4/1994 | Johnson et al. | |
| 5,328,077 A | 7/1994 | Lou | |
| 5,344,399 A * | 9/1994 | DeVries | 604/96.01 |
| 5,364,406 A | 11/1994 | Sewell, Jr. | |
| 5,366,479 A | 11/1994 | McGarry | |
| 5,370,662 A | 12/1994 | Stone et al. | |
| 5,372,146 A | 12/1994 | Branch | |
| 5,377,668 A | 1/1995 | Ehmsen et al. | |
| 5,379,933 A | 1/1995 | Green et al. | |
| 5,387,221 A * | 2/1995 | Bisgaard | 606/148 |
| 5,391,170 A | 2/1995 | McGuire et al. | |
| 5,411,506 A | 5/1995 | Goble et al. | |
| 5,417,712 A | 5/1995 | Whittaker et al. | |
| 5,423,860 A | 6/1995 | Lizardi et al. | |
| 5,425,489 A | 6/1995 | Shichman et al. | |
| 5,441,502 A | 8/1995 | Bartlett | |
| 5,443,482 A | 8/1995 | Stone et al. | |
| 5,464,407 A | 11/1995 | McGuire | |
| 5,474,543 A | 12/1995 | McKay | |
| 5,478,344 A | 12/1995 | Stone et al. | |
| 5,480,409 A | 1/1996 | Riza | |
| 5,500,001 A | 3/1996 | Trott | |
| 5,501,683 A | 3/1996 | Trott | |
| 5,501,688 A | 3/1996 | Whiteside et al. | |
| 5,507,754 A | 4/1996 | Green et al. | |
| 5,520,696 A | 5/1996 | Wenstrom, Jr. | |
| 5,520,700 A | 5/1996 | Beyar et al. | |
| 5,522,843 A | 6/1996 | Zang | |
| 5,522,845 A | 6/1996 | Wenstrom, Jr. | |
| 5,544,664 A | 8/1996 | Benderev et al. | |
| 5,556,092 A * | 9/1996 | Theken | 473/538 |
| 5,571,117 A | 11/1996 | Ahn | |
| 5,573,548 A | 11/1996 | Nazre et al. | |
| 5,578,057 A | 11/1996 | Wenstrom et al. | |
| 5,582,188 A | 12/1996 | Benderev et al. | |
| 5,584,695 A | 12/1996 | Lal Sachdeva et al. | |
| 5,584,835 A | 12/1996 | Greenfield | |
| 5,591,163 A | 1/1997 | Thompson | |
| 5,591,207 A | 1/1997 | Coleman | |
| 5,607,432 A | 3/1997 | Fucci | |
| 5,611,515 A | 3/1997 | Benderev | |
| 5,611,801 A * | 3/1997 | Songer | 606/73 |
| 5,618,308 A | 4/1997 | Holmes et al. | |
| 5,618,314 A | 4/1997 | Harwin et al. | |
| 5,620,012 A | 4/1997 | Benderev et al. | |
| 5,643,288 A | 7/1997 | Thompson | |
| 5,643,320 A | 7/1997 | Lower et al. | |
| 5,653,373 A | 8/1997 | Green et al. | |
| 5,662,654 A | 9/1997 | Thompson | |
| 5,662,658 A | 9/1997 | Wenstrom, Jr. | |
| 5,674,247 A | 10/1997 | Sohn | |
| 5,681,352 A | 10/1997 | Clancy, III et al. | |
| 5,683,418 A | 11/1997 | Luscombe et al. | |
| 5,690,649 A | 11/1997 | Li | |
| 5,690,677 A | 11/1997 | Schmieding et al. | |
| 5,697,931 A | 12/1997 | Thompson | |
| 5,702,397 A | 12/1997 | Goble et al. | |
| 5,702,415 A | 12/1997 | Matthai et al. | |
| 5,725,529 A | 3/1998 | Nicholson et al. | |
| 5,725,557 A | 3/1998 | Gatturna et al. | |
| 5,728,113 A | 3/1998 | Sherts | |
| 5,746,763 A | 5/1998 | Benderev et al. | |
| 5,749,884 A | 5/1998 | Benderev et al. | |
| 5,752,963 A | 5/1998 | Allard et al. | |
| 5,766,221 A | 6/1998 | Benderev et al. | |
| 5,782,862 A | 7/1998 | Bonutti | |
| 5,785,640 A | 7/1998 | Kresch et al. | |
| 5,797,918 A | 8/1998 | McGuire et al. | |
| 5,797,956 A | 8/1998 | Furnish et al. | |
| 5,807,403 A | 9/1998 | Beyar et al. | |
| 5,813,408 A | 9/1998 | Benderev et al. | |
| 5,814,051 A | 9/1998 | Wenstrom, Jr. | |
| 5,814,071 A | 9/1998 | McDevitt et al. | |
| 5,814,072 A | 9/1998 | Bonutti | |
| 5,827,263 A | 10/1998 | Furnish et al. | |
| 5,827,291 A | 10/1998 | Fucci et al. | |
| 5,830,231 A | 11/1998 | Geiges, Jr. | |
| 5,836,314 A | 11/1998 | Benderev et al. | |
| 5,836,315 A | 11/1998 | Benderev et al. | |
| 5,842,478 A | 12/1998 | Benderev et al. | |

| | | |
|---|---|---|
| 5,846,221 A | 12/1998 | Snoke et al. |
| 5,849,004 A | 12/1998 | Bramlet |
| 5,851,219 A | 12/1998 | Goble et al. |
| 5,860,425 A | 1/1999 | Benderev et al. |
| 5,860,953 A | 1/1999 | Snoke et al. |
| 5,868,747 A | 2/1999 | Ochoa et al. |
| 5,868,789 A | 2/1999 | Huebner |
| 5,871,503 A | 2/1999 | Bartlett |
| 5,911,722 A | 6/1999 | Adler et al. |
| 5,913,818 A | 6/1999 | Co et al. |
| 5,935,102 A | 8/1999 | Bowden et al. |
| 5,938,686 A | 8/1999 | Benderev et al. |
| 5,972,000 A | 10/1999 | Beyar et al. |
| 5,988,171 A | 11/1999 | Sohn et al. |
| 5,993,458 A * | 11/1999 | Vaitekunas et al. ......... 606/104 |
| 6,001,104 A | 12/1999 | Benderev et al. |
| 6,007,531 A | 12/1999 | Snoke et al. |
| 6,017,322 A | 1/2000 | Snoke et al. |
| 6,030,402 A | 2/2000 | Thompson et al. |
| 6,042,583 A | 3/2000 | Thompson et al. |
| 6,053,935 A * | 4/2000 | Brenneman et al. ........ 606/232 |
| 6,056,688 A | 5/2000 | Benderev et al. |
| 6,077,216 A | 6/2000 | Benderev et al. |
| 6,129,740 A * | 10/2000 | Michelson ................. 606/205 |
| 6,171,330 B1 * | 1/2001 | Benchetrit ................. 606/219 |
| 6,203,507 B1 | 3/2001 | Wadsworth et al. |
| 6,206,870 B1 * | 3/2001 | Kanner ....................... 604/523 |
| 6,228,024 B1 | 5/2001 | Co et al. |
| 6,241,736 B1 | 6/2001 | Sater et al. |
| 6,280,379 B1 | 8/2001 | Resnick |
| 6,299,624 B1 | 10/2001 | Cuschieri et al. |
| 6,299,625 B1 | 10/2001 | Bacher |
| 6,358,268 B1 | 3/2002 | Hunt et al. |
| 6,436,122 B1 | 8/2002 | Frank et al. |
| 6,447,527 B1 | 9/2002 | Thompson et al. |
| D466,213 S * | 11/2002 | Snitkin et al. ............. D24/145 |
| 6,544,273 B1 * | 4/2003 | Harari et al. ................ 606/151 |
| 6,730,110 B1 * | 5/2004 | Harari et al. ................ 606/213 |
| 2001/0010008 A1 | 7/2001 | Gellman et al. |
| 2001/0023356 A1 | 9/2001 | Raz et al. |
| 2001/0027321 A1 | 10/2001 | Gellman et al. |
| 2002/0035369 A1 * | 3/2002 | Beyar et al. ................ 606/104 |
| 2002/0183762 A1 * | 12/2002 | Anderson et al. ........... 606/104 |

FOREIGN PATENT DOCUMENTS

| | | |
|---|---|---|
| EP | 0 241 240 A2 | 10/1987 |
| EP | 0 281 763 A2 | 9/1988 |
| EP | 0 558 993 A2 | 9/1993 |
| EP | 0 599 772 A1 | 6/1994 |
| EP | 0 686 373 A1 | 12/1995 |
| EP | 1 021 991 A1 | 7/2000 |
| FR | 2718012 | 10/1995 |
| FR | 2739016 | 3/1997 |
| GB | 1044633 | 10/1966 |
| GB | 2268690 | 1/1994 |
| WO | 89/10096 | 11/1989 |
| WO | 92/16152 | 10/1992 |
| WO | 93/10715 | 6/1993 |
| WO | 93/19678 | 10/1993 |
| WO | 96/25887 | 8/1996 |
| WO | 96/28100 | 9/1996 |
| WO | 97/06731 | 2/1997 |
| WO | 97/30638 | 8/1997 |
| WO | 97/41792 | 11/1997 |
| WO | 98/12971 | 4/1998 |
| WO | WO0040158 A2 * | 7/2000 ................. 606/205 |
| WO | WO-01/28439 A1 | 4/2001 |
| WO | WO-02/098301 A1 | 12/2002 |

OTHER PUBLICATIONS

Benderev et al., A New Endoscopic Bladder Neck Suspension for the Outpatient Treatment of Stress Urinary Incontinence, (video v-40) J. Urology 149: 197A (1993).

Benderev, A Modified Percutaneous Outpatient Bladder Neck Suspension System, J. Urology 152: 2316-2320 (1994).

Petros et al., The Intravaginal Slingplasty Operation, a Minimally Invasive Technique for Cure of Urinary Incontinence in the Female, Aust. NZ 1. Obstet. Gynaecol. 36: 453-461 (1996).

Robertson et al., Soft Tissue Fixation to Bone, Am. J. Sports Med. 14: 398-403 (1986).

* cited by examiner

BONE ANCHOR IMPLANTATION DEVICE

TECHNICAL FIELD

The invention relates to devices for manually implanting a bone anchor into bone.

BACKGROUND OF THE INVENTION

Female Stress Urinary Incontinence (FSUI) is a disorder that can interfere with daily activity and impair the quality of life of women. In approximately 30% of the women suffering from FSUI, incontinence is caused by intrinsic sphincter deficiency (ISD), a condition in which the valves of the urinary sphincter do not properly coapt. In approximately another 30% of FSUI sufferers, incontinence is caused by hypermobility, a condition in which the muscles around the bladder relax, causing the bladder neck and proximal urethra to rotate and descend in response to increases in intraabdominal pressure. Hypermobility may be the result of pregnancy or other conditions which weaken the muscles. Urinary incontinence may also be caused by a combination of ISD and hypermobility. Other causes of urinary incontinence include birth defects, disease, injury, aging, and urinary tract infection.

Numerous approaches for treating urinary incontinence are available. For example, several procedures for stabilizing and/or slightly compressing the bladderneck or urethra to prevent the leakage of urine have been developed. The stabilizing or compressive force may be applied directly by sutures passing through the soft tissue surrounding the urethra or, alternatively, may be applied by means of a sling suspended by sutures. In some procedures bone anchors are inserted into the pubic bone or symphysis pubis in order to anchor the sutures to the bone. The suture or sling is anchored to the bone by one or more bone anchors and the support provided improves the incontinence condition.

The instruments used to insert bone anchors are designed to be inserted transvaginally and to position the bone anchor so that a retrograde or pulling force is applied for insertion of the anchor into the bone. However, the optimal configuration or position of the handle of such an instrument for insertion of the device into the vagina is not necessarily the optimal handle position for providing a retrograde force for implanting the bone anchors into the bone. For example, the fixed handle position of conventional bone anchor devices is particularly awkward when treating obese patients.

SUMMARY OF THE INVENTION

The present invention relates to devices and methods for inserting anchors, such as bone anchors, into a bone or tissue.

In one aspect, a device is provided for manually implanting a bone anchor into a bone; the device includes a handle, a shaft, and a bone anchor-mount. The handle has a proximal end and a distal end. The shaft has a first end and a second end, and may be straight with a bend at its second end, or may instead be hook-shaped. The first end of the shaft is connected to the distal end of the handle. The bone anchor-mount is connected to the second end of the shaft and oriented toward the handle so that a bone anchor received within the mount may be implanted into a bone by applying a retrograde force using the handle. The handle may have at least one finger indentation at its distal end, thereby providing an ergonomic grip. For example, the handle may contain two, three, four or more finger indentations at its distal end. The handle may also be shaped to fit into a user's palm.

In another aspect, the invention provides a bone anchor implantation device with a handle that can be rotated relative to the longitudinal axis of the shaft during a bone anchor implantation procedure, to facilitate the insertion of the device into a body cavity and/or implantation of a bone anchor. For example, the device can be inserted into the vagina of a patient with the handle in one position, following which the handle can be rotated about the longitudinal axis of the device's shaft and locked into a second position, wherein the second position facilitates the application of a retrograde force or pulling action required for anchoring the bone anchor into a bone.

In a particular embodiment, the handle may be both rotatable and ergonomic.

In one version of the device, the handle may be rotatable between two angular positions and may contain a stop assembly for locking the handle in a first or a second angular position. For example, a representative stop assembly has an outer cylinder, an inner cylinder and a spring. The outer cylinder is fixed to the handle and aligned with the shaft, and includes a circumferential slit having a pair of diametrically opposed detents, for example. The inner cylinder is rotatably disposed within the outer cylinder and is also fixed to the first end of the shaft. The inner cylinder includes a drive pin extending horizontally through the inner and outer cylinders. The drive pin has a pair of ends, one or both of which are received within the outer cylinder's circumferential slit and seatable within the detent(s). The seating of the drive pin within the detent(s) prevents rotation of the outer cylinder with respect to the inner cylinder. The spring is disposed within the outer cylinder and urges the inner cylinder in a direction toward the bone anchor-mount. Compression of the spring releases the drive-pin ends from the detents, permitting rotation of the handle.

In this example, the handle is rotatable between first and second angular positions separated by about 180°, but the detents may be located to provide any desired angular displacement between stops as dictated by the application. The handle may be placed in the first angular position for insertion of the device into a cavity and rotated to the second angular position for implanting the bone anchor. The handle may also have additional angular stop positions.

The bone anchor-mount may comprise an outer cylinder, an inner cylinder, and a tapered bone anchor receptacle for releasably engaging a bone anchor. In one representative bone anchor-mount, the outer cylinder has a distal end and a proximal end. An annular shoulder is located at the proximal end of the outer cylinder. The inner cylinder is rigidly connected to the outer cylinder and extends proximally therefrom. The bone anchor receptacle is rigidly connected to the inner cylinder and extends proximally therefrom. The device may further comprise a protective sheath connected to the bone anchor-mount for isolating the bone anchor from contact with tissue prior to implantation of the bone anchor into a bone. The protective sheath may be axially movable relative to the bone anchor such that the bone anchor is exposed from the sheath as the bone anchor is pulled or pressed into a bone. In a preferred embodiment, the protective sheath is composed of a flexible material such as, for example, silicone or rubber.

In another aspect, the present invention provides a method for inserting a bone anchor releasably engaged to a bone anchor implantation device into a bone. The bone anchor implantation device is inserted, a bone anchor implantation site is located on the bone, and a retrograde force is applied to the bone anchor to implant the bone anchor into the bone. The handle may contain one or more finger indentations and may be in a first position for insertion of the device into a body cavity and rotated to a second position for implanting the bone anchor. The locating and implanting steps may be accomplished transvaginally. For procedures relating to FSUI, the bone anchor may be implanted in the posterior pubic bone or implanted lateral to the symphysis pubis and cephalad to the inferior edge of the pubic bone.

BRIEF DESCRIPTION OF THE DRAWINGS

In the drawings, like reference characters generally refer to the same parts throughout the different views. Also, the drawings are not necessarily to scale, emphasis being placed upon illustrating the principles of the invention.

DETAILED DESCRIPTION OF THE INVENTION

The present invention relates to a device for implanting a bone anchor into bone. It also relates to methods for improving or maintaining a patient's urinary continence in which bone anchors are inserted transvaginally into the posterior portion of the pubic bone or symphysis pubis.

A bone anchor implantation device in accordance with the invention may have an ergonomic handle which has at least one finger indentation in the distal end of the handle. The handle may have one, two, three or four or more finger indentations. In one version of this embodiment, the shaft may be attached to the handle between finger indentations.

A bone anchor implantation device in accordance with the invention may have a handle that can be rotated relative to the shaft of the device, facilitating bone anchor implantation by allowing a physician the flexibility of rotating the handle of the device during the procedure in order to optimize the angle of the bone anchor-mount and shaft relative to the physician's hand and the patient's body. For example, the design of the device allows it to be inserted into the vagina of a patient and to position the bone anchor on a bone and for the handle to be rotated about the longitudinal axis of the shaft of the device prior to providing the retrograde force required to implant the bone anchor into a bone. The form of the handle is not critical to its rotation, e.g., the handle does not need indentations for rotation.

The bone anchor-mount generally points toward the handle, such that the user can drive the bone anchor into the bone by simply pulling back on the handle and using the patient's body weight to provide an opposing force. Preferably, the longitudinal axis of the bone anchor-mount may be aligned with the longitudinal axis of the handle. A protective sheath may be attached to the bone anchor-mount such that the bone anchor is releasably engaged to the bone anchor-mount but enclosed within the protective sheath and isolated from tissue contact during placement of the device and prior to implantation.

Figure 1:
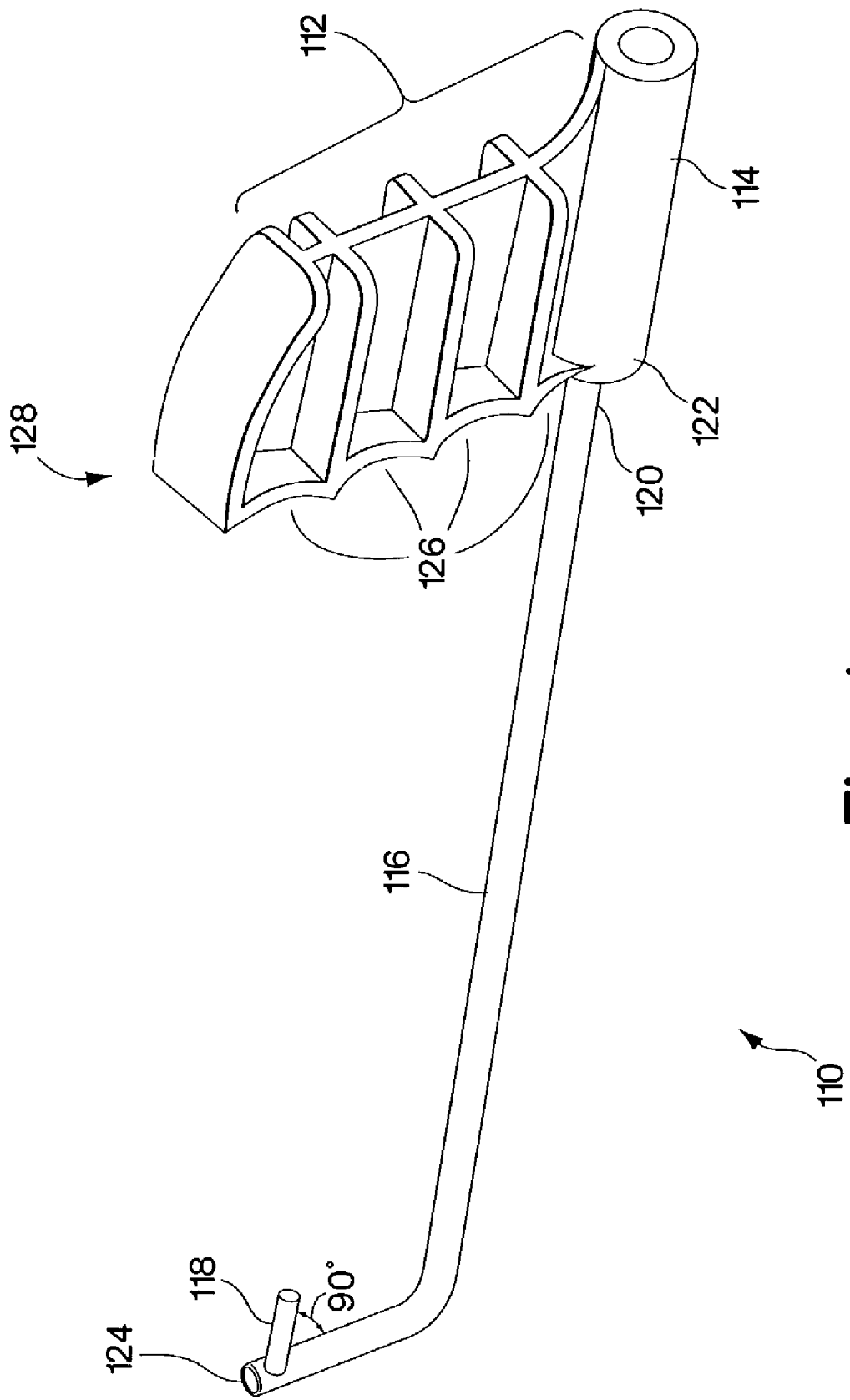
FIG. 1 is a perspective view of a bone anchor implantation device having an ergonomic handle and a shaft.
Figure 2:
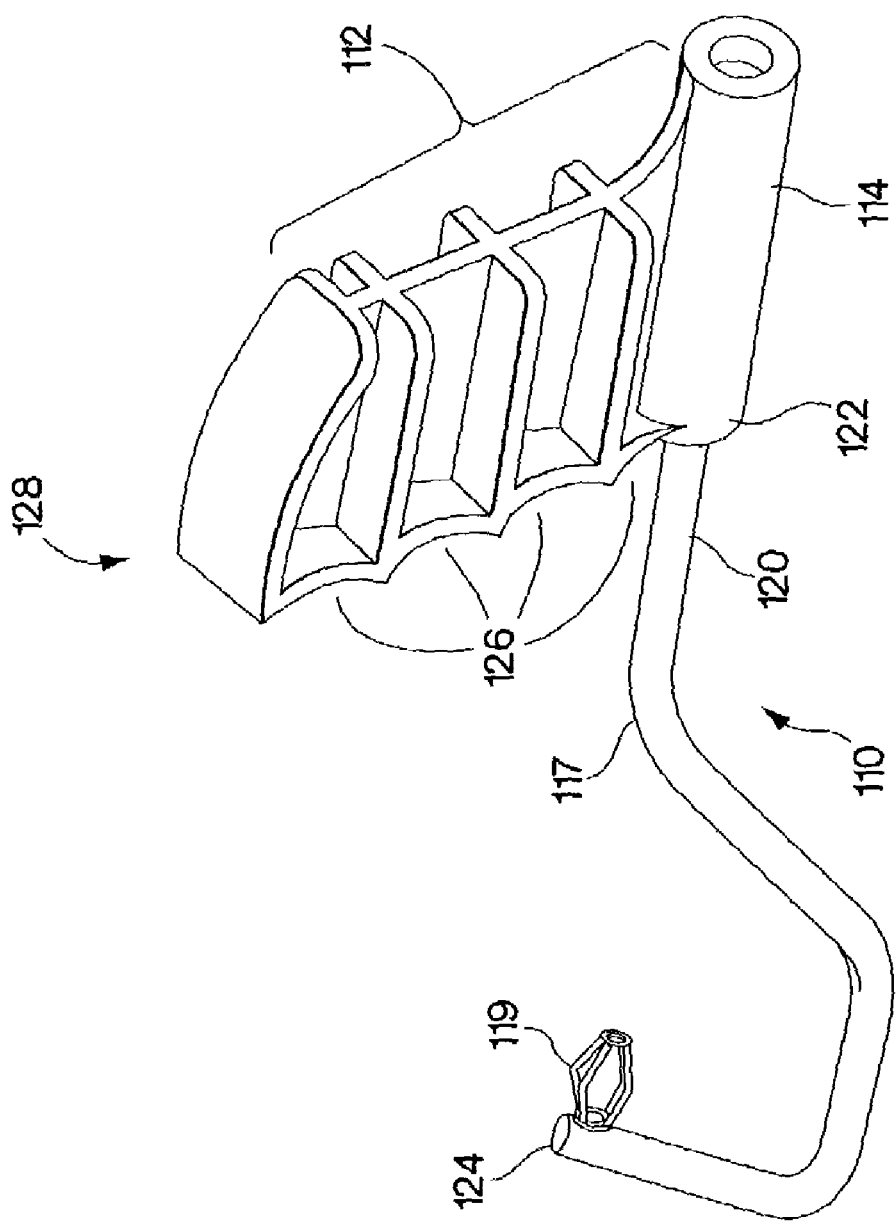
FIG. 2 is a perspective view of a bone anchor implantation device having an ergonomic handle and a bent shaft.

Referring to the two embodiment illustrated in FIGS. 1 and 2, the device 110 has a handle 112, a cylinder 114, a shaft 116, 117 and a bone anchor-mount 118, 119. The cylinder 114 is connected to, or forms a part of, the handle 112. The inner end 120 of the shaft 116, 117 is connected to the distal end 122 of the cylinder 114. The bone anchor-mount 118, 119 may be connected to the outer end 124 of the shaft 116, 117.

The handle 112 may be made of a variety of materials, such as plastic or metal. The shaft 116, 117 may be made of a variety of materials, such as stainless steel, one or more engineering plastics, fiber-bearing components, or other rigid materials. Preferably, the shaft 116, 117 is made of stainless steel.

The shaft 116 may be straight as illustrated, for example, in FIG. 1. Alternatively, the shaft 117 may be bent, as illustrated, for example, in FIG. 2 or may be arched or hooked, as illustrated, for example, in FIG. 3A.

The handle 112 may have at least one finger indentation 126 at its distal end 128. The physician's fingers may be seated in these indentations 126 during operation of the device. The finger indentations 126 are provided and positioned such that a physician has an improved grip for exerting a retrograde force for implanting a bone anchor. In the version illustrated in FIGS. 1 and 2, the handle 112 has four finger indentations 126 on its distal end 128.

The bone anchor-mount 118, 119 is able to releasably engage a bone anchor. In one embodiment of the invention, the bone anchor-mount 118, 119 is fixed perpendicular to the outer end 124 of the shaft 116, 117. The outer end 124 may be bent or otherwise angled so that the bone anchor-mount 118, 119 is substantially parallel to the shaft 116, 117. For example, FIG. 1 illustrates an embodiment of the invention in which the outer end 124 is bent at an angle of about 90° relative to the longitudinal axis of the shaft 116 and the bone anchor-mount 118 is parallel to the shaft 116. Alternatively, the outer end 124 may be angled more or less than about 90° relative to the longitudinal axis of the shaft 116, 117. The bone anchor-mount 118, 119 may be fixed to the shaft 116, 117 at an angle greater or less than 90°.

The bone anchor-mount 118, 119 may be oriented toward the handle 112 so that a bone anchor received within the bone anchor-mount 118, 119 may be implanted into a bone by applying a retrograde force (e.g., a pulling force) using the handle 112.

Figure 3A:
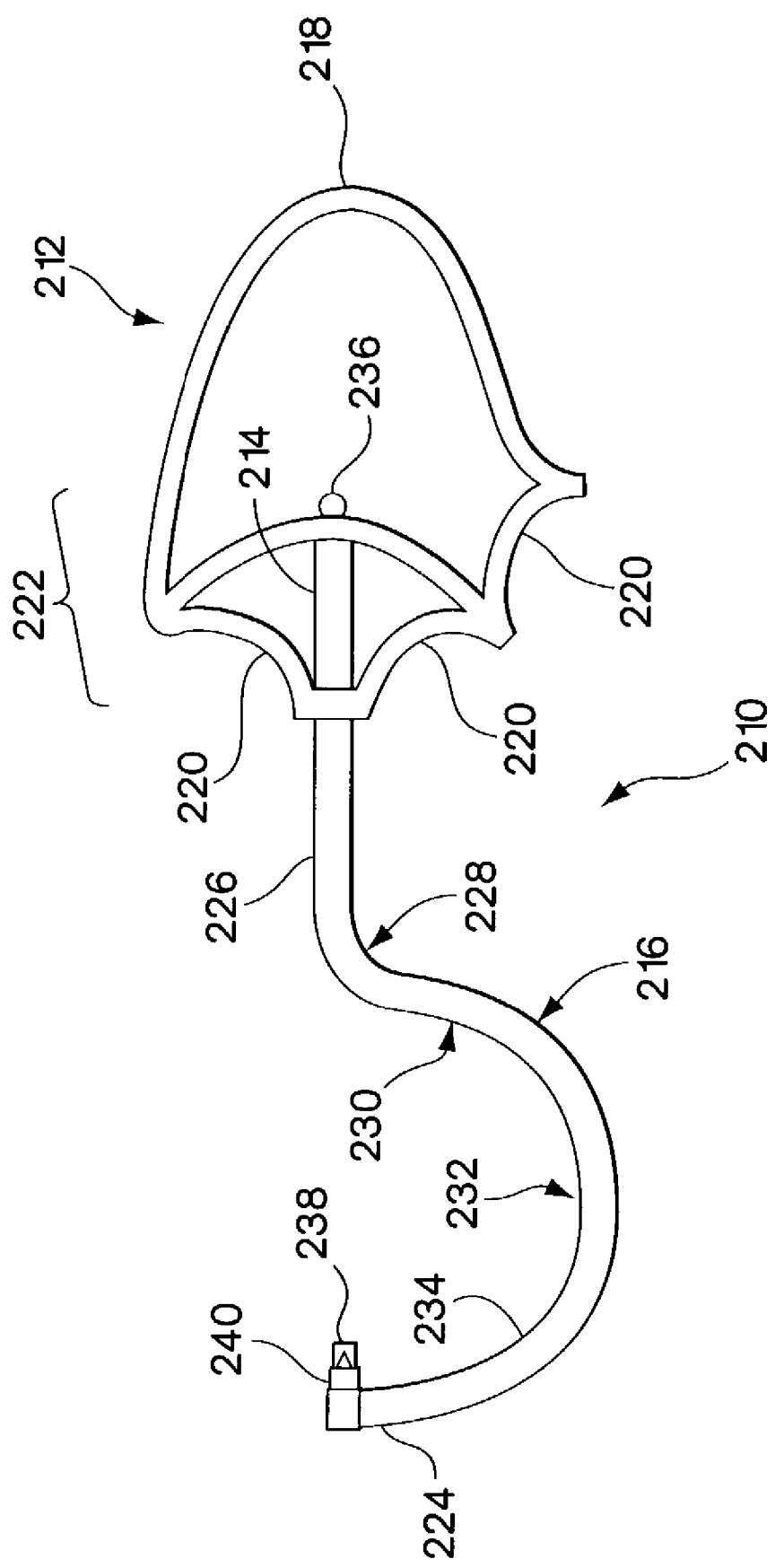
FIG. 3A is a side view of a bone anchor implantation device having an ergonomic handle and a hooked shaft.
Figure 3B:
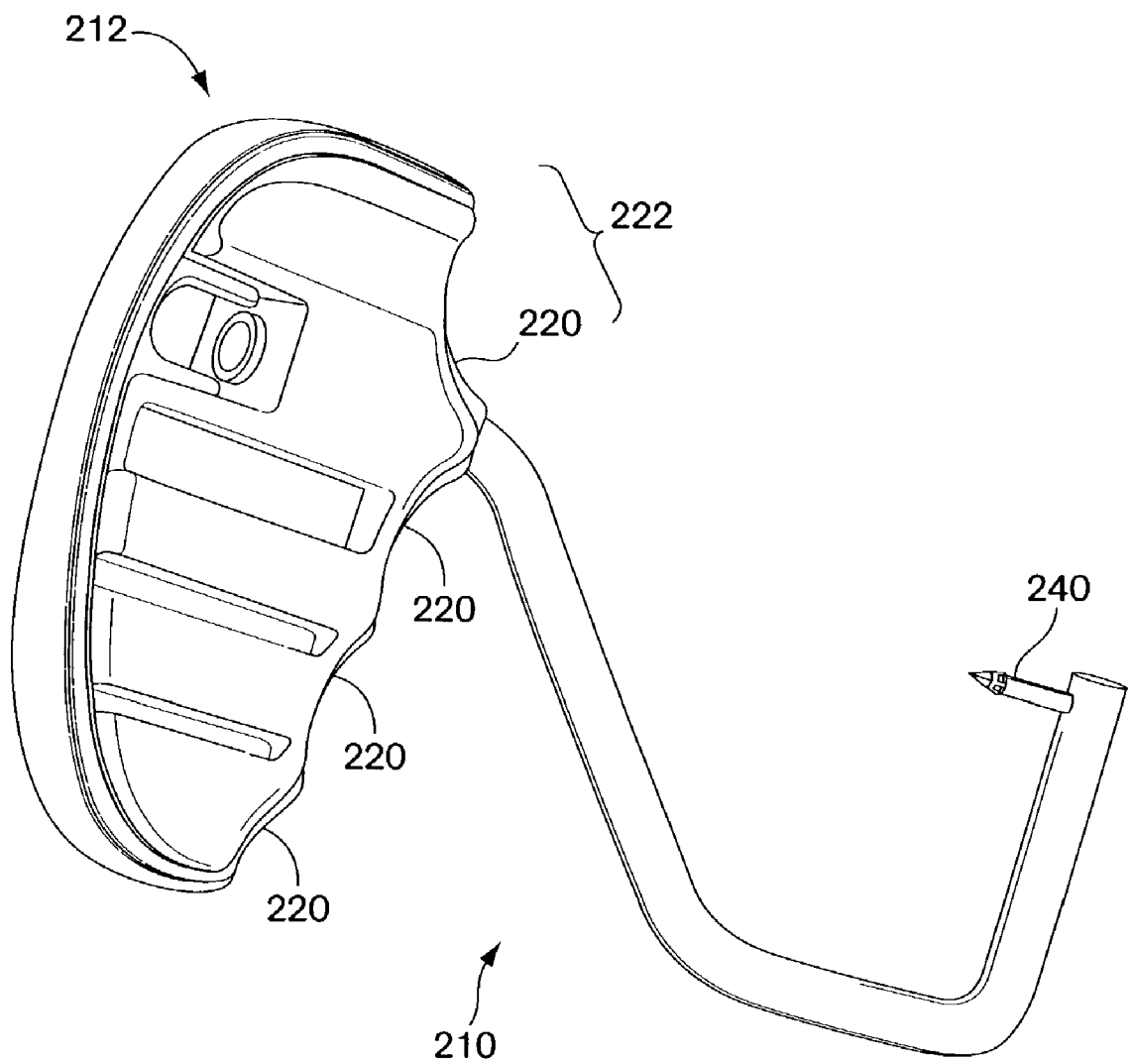
FIG. 3B is a perspective view of a bone anchor implantation device having an ergonomic handle and a bent shaft.
Figure 3C:
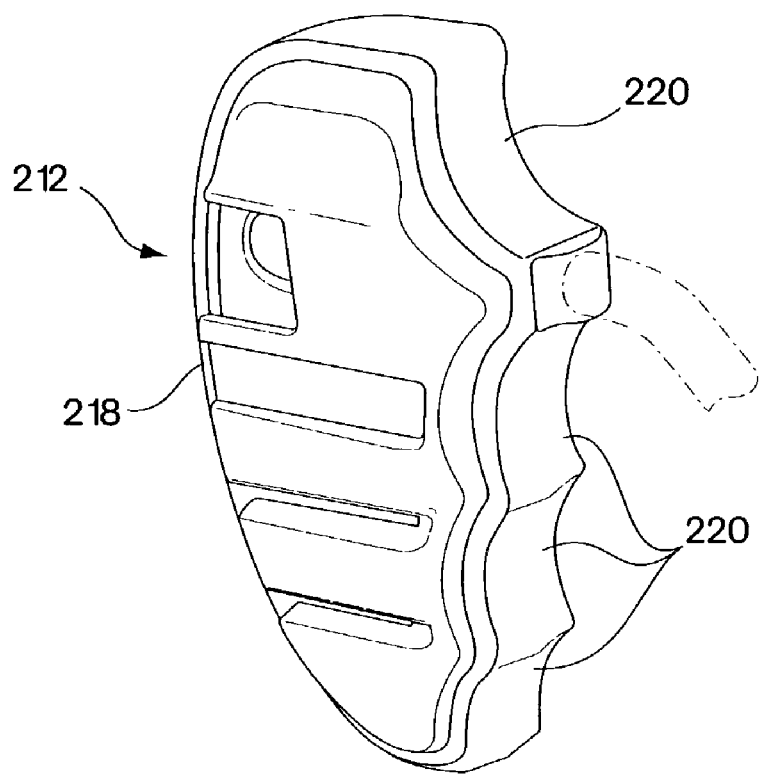
FIG. 3C is a perspective view of the handle of the device in FIG. 3B.
Figure 3D:
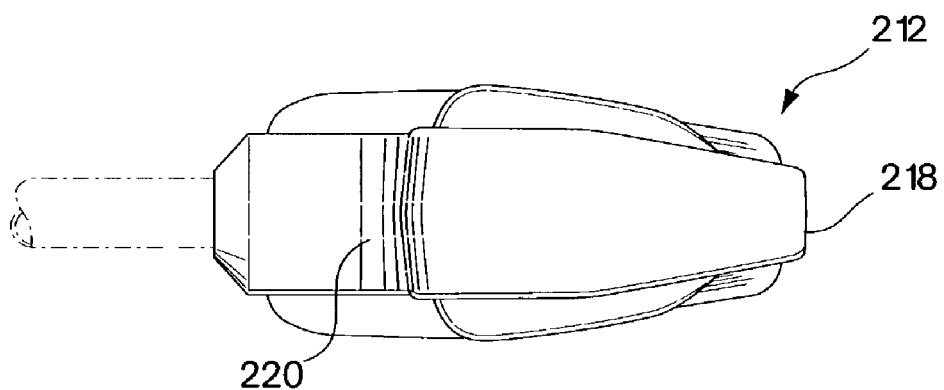
FIG. 3D is a top view of the handle of the device in FIG. 3B.
Figure 3E:
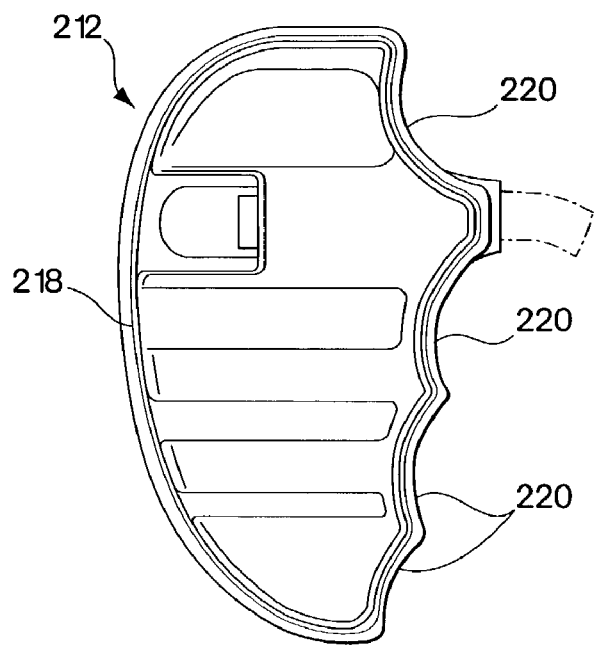
FIG. 3E is a side view of the handle of the device in FIG. 3B.
Figure 3F:
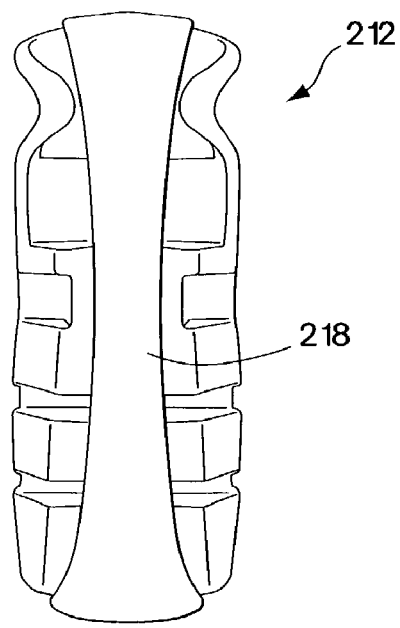
FIG. 3F is a rear view of the handle of the device in FIG. 3B.
Figure 3G:
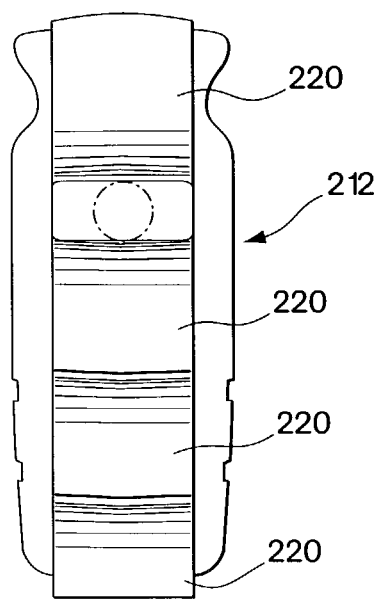
FIG. 3G is a front view of the handle of the device in FIG. 3B.
Figure 3H:
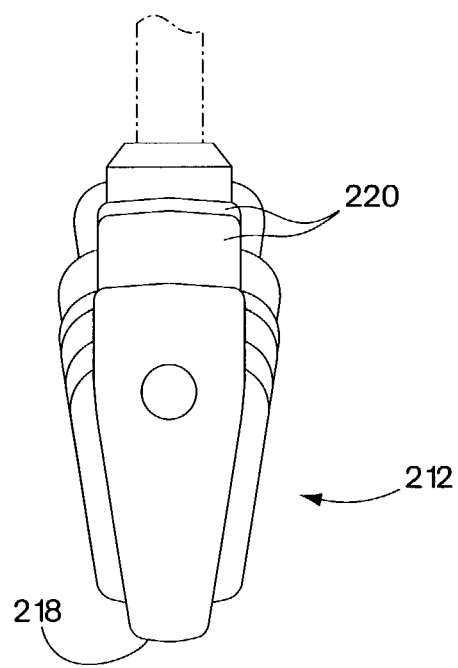
FIG. 3H is a bottom view of the handle of the device in FIG. 3B.

Referring to the device 210 of FIG. 3A, a handle 212 having a different configuration is attached to the inner end 214 of the shaft 216. The handle is also designed to ergonomically fit the fingers of a physician's hand. As illustrated, the handle contains three finger indentations 220 at its distal end 222. Alternatively, the handle 212 may contain two, four or more finger indentations 220 at its distal end 222. In addition, the proximal end 218 of the handle 212 is shaped to fit a physician's palm. FIGS. 3B–3H illustrate various views of a preferred embodiment of the invention in which the handle 212 has three lower finger indentations 220 and one upper finger indentation 220.

Referring to FIG. 3A, the shaft 216 comprises an inner end 214 and an outer end 224, a straight proximal section 226, a first generally curved section 228 distal to the straight proximal section 226, a second generally curved section 230 distal to the first curved section 228, a third generally curved section 232 distal to the second curved section 230, and a fourth generally curved section 234 distal to the third curved section 232. The straight proximal section 226 of the shaft 216 may be from about 3 inches to about 6 inches in length, depending on the application. For FSUI procedures, the straight proximal section 226 is preferably from about 4 inches to about 5 inches in length and more preferably about 4.5 inches in length. One of skill in the art will appreciate that the shaft 216 could also comprise a series of straight segments angled relative to one another to form a hook.

The inner end 214 of the shaft 216 may be connected to the distal end 222 of the handle 212 in between finger indentations 220. Alternatively, the straight proximal section 226 may pass through a lumen (not shown) extending through the distal end 222 of the handle 212. The inner end 214 may have a threaded bore which may be adapted to receive a screw 236 which secures the shaft 216 to the handle 212. If desired, a washer (not shown) may be placed between the distal end 222 of the handle 212 and the screw 236. Those skilled in the art will appreciate that a variety of other means for securing the shaft 216 to the handle 212 may be employed. For example, a plastic handle may be formed over the shaft such that the shaft is integral with the handle. It should be stressed that the benefits of an ergonomic handle 112, as illustrated in FIG. 1, and an ergonomic handle 212, as illustrated in FIG. 3, may be utilized in devices that do not permit rotation.

With continued reference to FIG. 3A, the handle 212 defines an axis at the proximal end of the anchor implantation device 210, and then moving distally from the handle 212 the shaft 216 first curves away from the axis of the handle and then back toward the axis of the handle 212. The outer end 224 of the shaft 216 is preferably located in the vicinity of the axis of the handle 212. In some preferred embodiments, the shaft 216 at the outer end 224 is generally perpendicular to the axis of the handle or can actually curve back toward the handle 212. For FSUI applications, the distance from the distal end 222 of the handle 212 to the tip of the bone anchor-mount 238 measured along the longitudinal axis of the handle 212 is preferably about 3 and ⅜ inches; the distance from the distal end of the handle 212 to the base of the bone anchor-mount 240 is about 4 inches; and the distance of a line perpendicular to the longitudinal axis of the handle 212 extending from the bottom of the third curved section 232 is about 2 inches.

A bone anchor-mount 240 may be attached to the outer end 224 of the shaft 216. The bone anchor-mount 240 may be oriented at an angle from about 60° to about 120° relative to the outer end 224 of the shaft 216. For FSUI applications, the bone anchor-mount 240 is preferably oriented at an angle from about 80° to about 100° relative to the outer end 224 of the shaft 216, and more preferably at an angle of approximately 90°.

Figure 4:
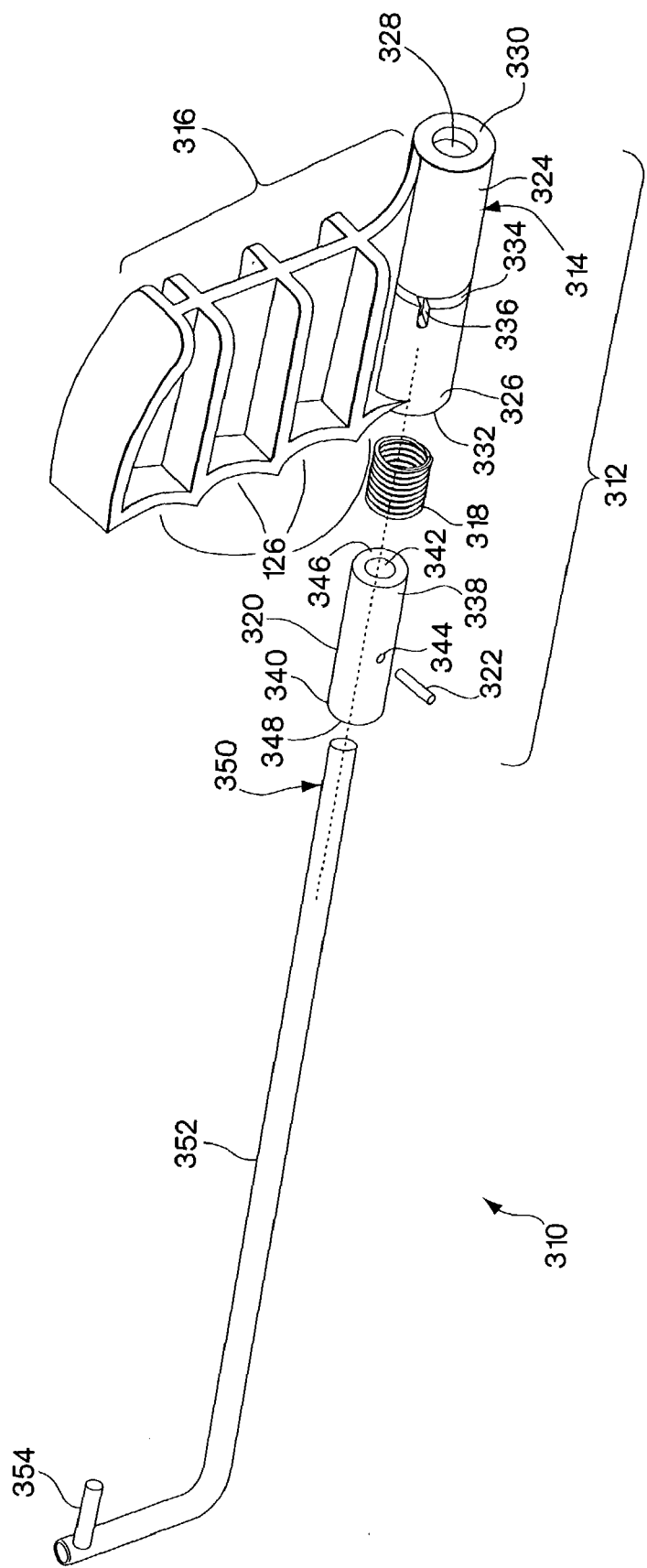
FIG. 4 is an exploded view of the components of a rotatable bone anchor implantation device having an ergonomic handle.
Figure 5:
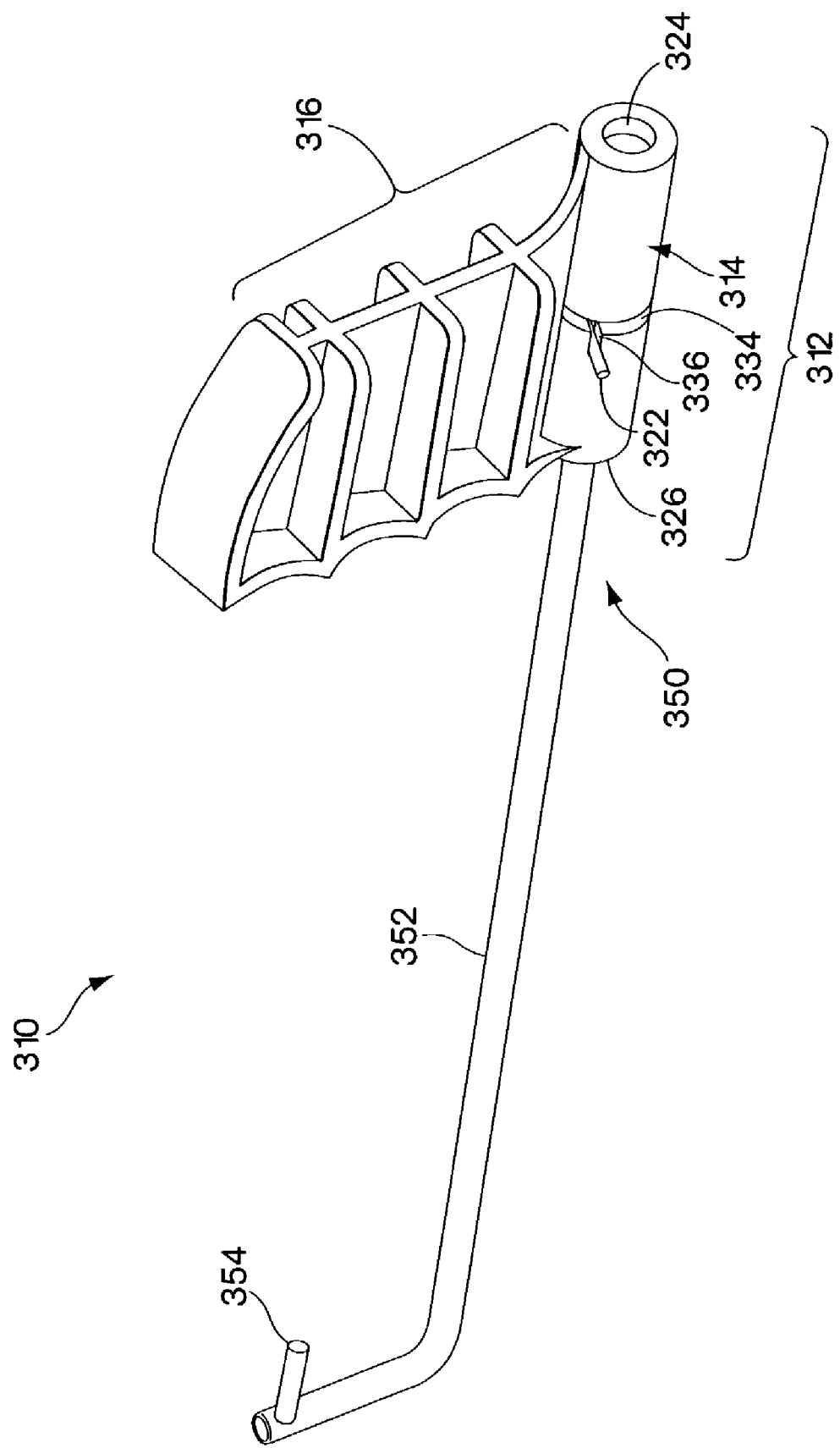
FIG. 5 is a perspective view of a rotatable bone anchor implantation device with the handle in a first angular position.
Figure 6:
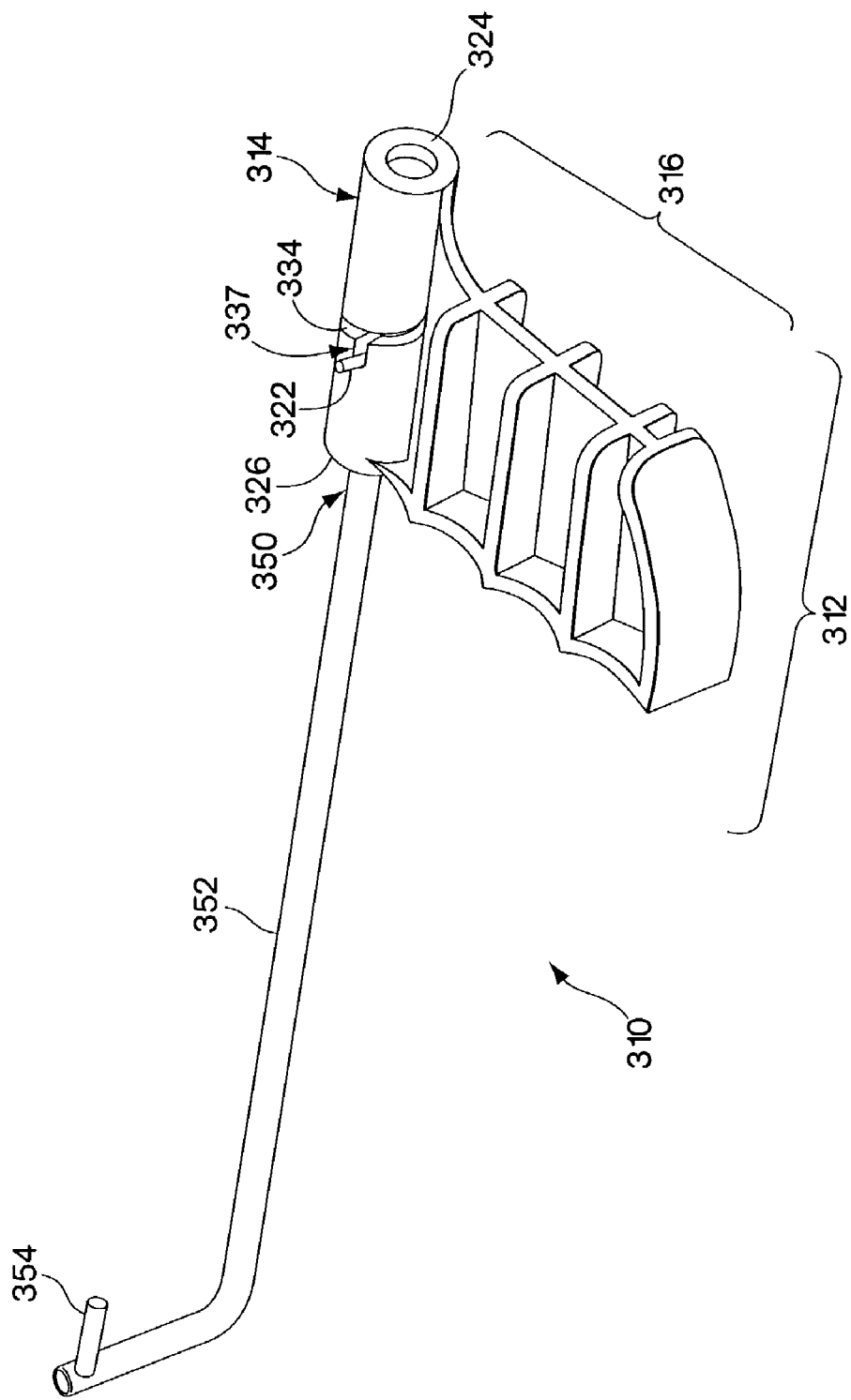
FIG. 6 is a perspective view of a rotatable bone anchor implantation device with the handle in a second angular position.

In another version of the invention, illustrated for example in FIGS. 4–6, the handle of the bone anchor delivery device may be rotatable about the longitudinal axis of the shaft. The device 310 has a stop assembly 312 operable within the cylinder 314, which is located at the base of the handle 316. The stop assembly 312 retains the handle 316 in any of two or more angular positions.

Referring to FIG. 4, the stop assembly 312 includes a cylinder 314, a spring 318, a cylindrical plug 320, and a drive pin 322. The cylinder 314 has a proximal end 324, a distal end 326, a lumen 328, a proximal shoulder 330, a distal shoulder 332, a circumferential slit 334 and one or more detents 336 within the slit 334. The plug 320 has a proximal end 338, a distal end 340, a drive pin aperture 344 for receiving the drive pin 322, a proximal face 346, and a distal face 348. The plug 320 may have a lumen 342. The distal end 340 of the plug 320 is fixed to the near end 350 of the shaft 352. The drive pin 322 is received within the drive pin aperture 344 but not fully, so that it protrudes beyond the radial extent of the plug 320. Alternatively, the aperture 344 may extend fully through the plug 320, and the drive pin 322 may have a length greater than the diameter of the plug 320, so that each end of the drive pin 322 protrudes beyond the radial extent of the plug 320. Alternatively, plug 320 may contain more than one aperture and receive more than one drive pin 322.

The plug 320 is spring loaded into the cylinder 314, and the drive pin 322 is introduced into the drive pin aperture 344 so that it engages with (i.e., is movable within) the circumferential slit 334 in cylinder 314. The distal face 348 of the plug 320 is retained behind the distal shoulder 332 of the cylinder 314, thereby preventing plug 320 from exiting the cylinder 314, notwithstanding the force applied by spring 318. The spring 318 is disposed between the proximal face 346 of the plug 320 and the proximal shoulder 330 of the cylinder 314. The spring 318 urges the plug 320 in a direction toward the bone anchor-mount 354.

The spring 318 may have a resistance of from about 5 to about 35 pounds. Preferably, the spring 318 has a resistance from about 15 to about 25 pounds, and more preferably, about 20 pounds. Those skilled in the art will appreciate that the anchor implantation device may also be adapted to include a force indicating spring in the handle.

The handle 316 may be rotatable between first and second angular positions, which are dictated by the placement of detents 336 in the cylinder 314. When the drive pin 322 is seated within the detent 336, no rotation is possible, and the spring 318 retains the seating of the drive pin 322 until the handle 316 is driven forward, compressing the spring 318. When the spring 318 is compressed, the drive pin 322 is released from the detent 336 and is free to travel within the circumferential slit 334, thereby allowing the handle 316 to be rotated about the plug 320. The handle 316 may be rotated until the spring 318 locks or seats the drive pin 322 into one or more detents 336, thereby preventing further rotation of the handle 316 with respect to the shaft 352. In one version of the device, two detents 336 are diametrically opposed along the circumferential slit 334 of the cylinder 314.

The drive pin 322 may engage one detent in the cylinder 314 if only one end of the drive pin 322 extends beyond the plug 320. Alternatively, the drive pin 322 may engage two detents 336 in the cylinder 314 if both ends of the drive pin 322 extend beyond the plug 320 and through the circumferential slit 334. There may be more detents 336 along the circumferential slit 334, so that the handle 316 may be rotated among more than two angular positions. There may also be more than one drive pin 322; for example, a cross-shaped drive pin may be used to simultaneously be seated in four detents 336.

As illustrated in FIG. 5, the drive pin 322 is seatable within detent(s) 336 and the handle 316 is in a first angular position. FIG. 6 illustrates the device shown in FIG. 5 after rotation of the handle 316 to a second angular configuration, with the drive pin 322 seated within a second detent (or detents) 337. The first and second angular positions may be, for example, about 180° apart. Of course, depending on the envisioned application, the first and second angular positions may be more or less than about 180° apart.

Figure 7:
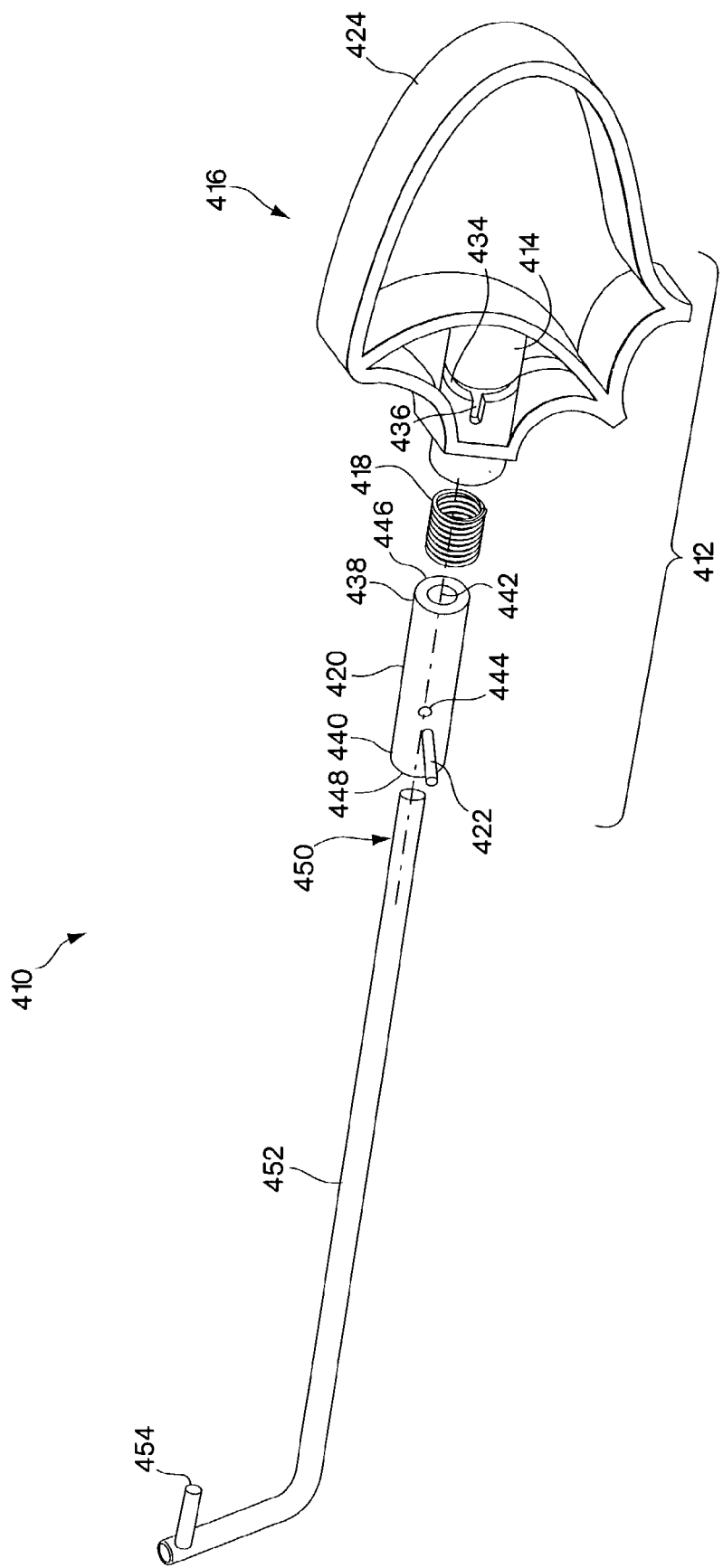
FIG. 7 is an exploded view of the components of a rotatable bone anchor implantation device having an ergonomic handle.
Figure 8:
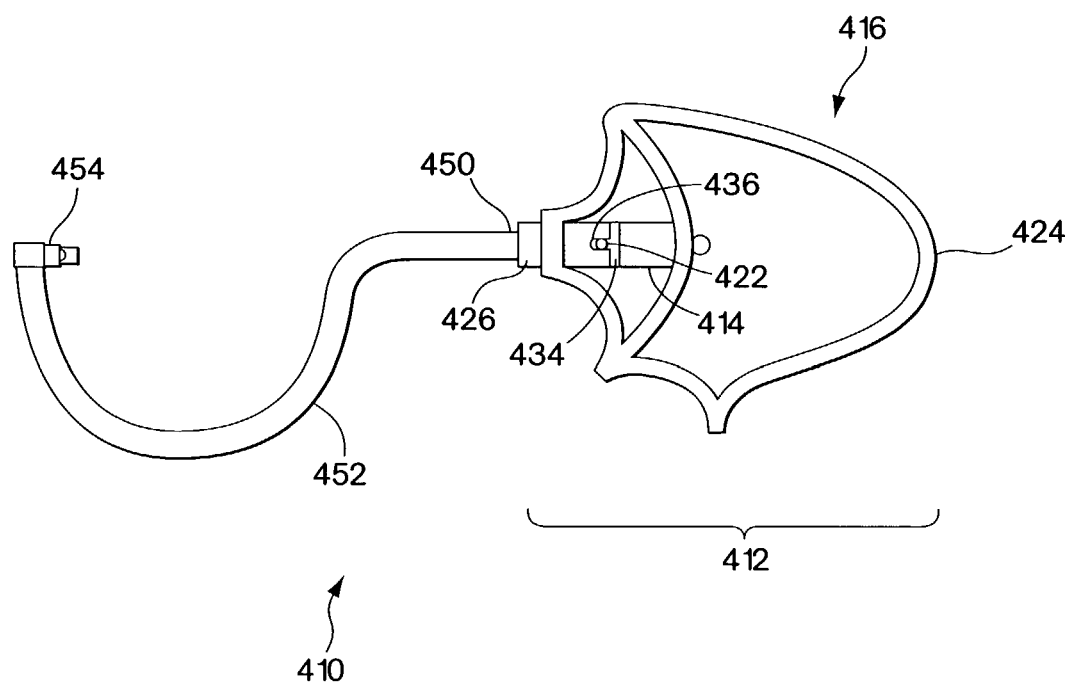
FIG. 8 is a side view of a rotatable bone anchor implantation device with the handle in a first angular position.
Figure 9:
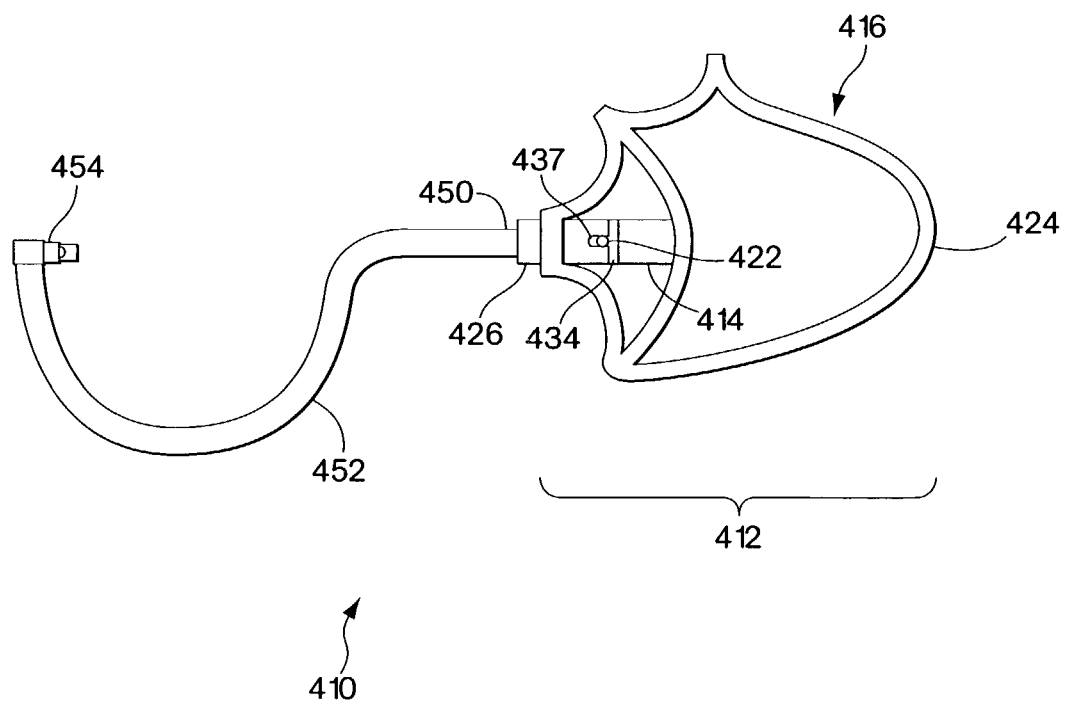
FIG. 9 is a side view of a rotatable bone anchor implantation device with the handle in a second angular position.

In a version of the invention as illustrated to FIGS. 7–9, a rotatable handle 416 may have a different configuration, in that it may be attached to the inner end 414 of the shaft 452. The handle may be designed to ergonomically fit the fingers of a physician's hand, as in the non-rotatable device of FIG. 3. The device 410 is rotatable in a similar fashion as that described for the device illustrated in FIGS. 4–6.

Referring to FIG. 7, the handle 416 may be rotatable between first and second angular positions, which are dictated by the placement of detents 436 in the cylinder 414. When the drive pin 422 is seated within the detent 436, no rotation is possible, and the spring 418 retains the seating of the drive pin 422 until the handle 416 is driven forward, compressing the spring 418. When the spring 418 is compressed, the drive pin 422 is released from the detent 436 and is free to travel within the circumferential slit 434, thereby allowing the handle 416 to be rotated about the plug 420. The handle 416 may be rotated until the spring 418 locks or seats the drive pin 422 into one or more detents 436, thereby preventing further rotation of the handle 416 with respect to the shaft 452. In one version of the device, two detents 436, 437 are diametrically opposed on along the circumferential slit 434 of the cylinder 414.

The drive pin 422 may engage one detent in the cylinder 414 if only one end of the drive pin 422 extends beyond the plug 420. Alternatively, the drive pin 422 may engage two detents 436, 437 in the cylinder 414 if both ends of the drive pin 422 extend beyond the plug 420 and through the circumferential slit 434. There may be more detents 436, 437 along the circumferential slit 434, so that the handle 416 may be rotated among more than two angular positions. There may also be more than one drive pin 422; for example, a cross-shaped drive pin may be used to simultaneously be seated in four detents 436.

As illustrated in FIG. 8, the drive pin 422 is seatable within detent(s) 436, 437 and the handle 416 is in a first angular position. FIG. 9 illustrates the device shown in FIG. 8 after rotation of the handle 416 to a second angular configuration, with the drive pin 422 seated within a second detent(s) 437. The first and second angular positions may be, for example, about 180° apart. Of course, depending on the envisioned application, the first and second angular positions may be more or less than about 180° apart.

Figure 10:
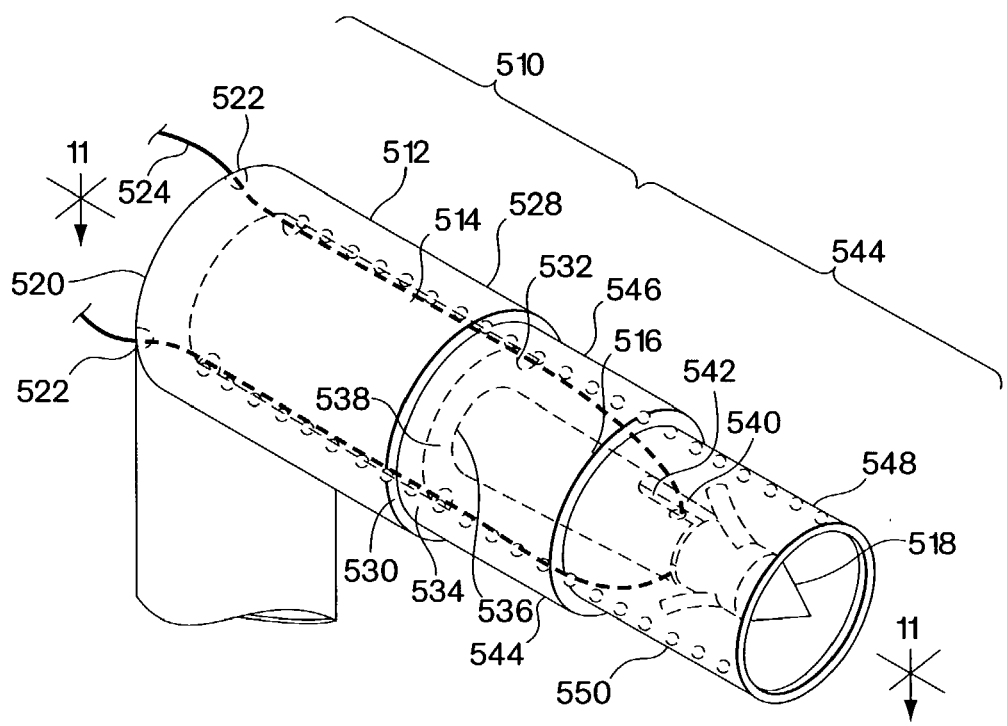
FIG. 10 is a perspective view of the bone anchor-mount.
Figure 11:
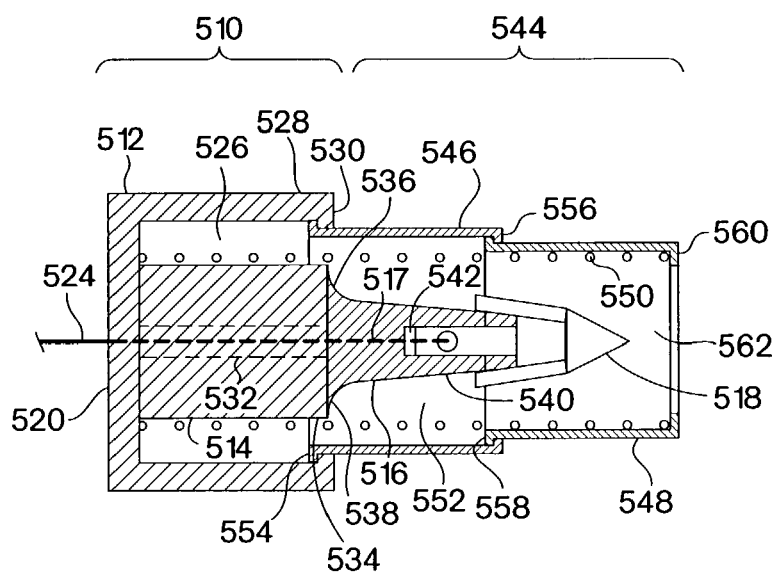
FIG. 11 is a cross-sectional view of the bone anchor-mount of FIG. 10.

Referring to FIGS. 10 and 11, the bone anchor-mount 510 may comprise an outer cylinder 512, an inner cylinder 514, and a tapered bone anchor receptacle 516 for releasably engaging a bone anchor 518. The bone anchor used may be the bone anchor disclosed in the U.S. Pat. No. 5,527,342, the entire disclosure of which is incorporated herein by reference.

The bone anchor-mount 510 and the bone anchor receptacle 516 are oriented so that the bone anchor 518 may be pointed in the general direction of the handle 512. In a particular embodiment, the axis of the bone anchor 518 may be generally aligned with the axis of the handle, with the bone anchor 518 pointed toward the handle.

The bone anchor-mount 510 may be fabricated from the same materials as the shaft 516 and may be attached to the shaft 516 by a variety of methods known to those skilled in the art, such as brazing. The distal end 520 of the outer cylinder 512 has a pair of holes 522 therein sized to accommodate a suture 524. The outer cylinder 512 may have a diameter from about 0.18 inches to about 0.6 inches. Preferably, the outer cylinder 512 has a diameter from about 0.25 inches to about 0.5 inches. More preferably, the outer cylinder 512 has a diameter of about 0.375 inches.

As best shown in FIG. 11, the outer cylinder 512 has a cavity 526 formed therein, creating a cup in the proximal region of the outer cylinder 512. The proximal end 528 of the outer cylinder 512 has an annular shoulder 530 thereon. The inner cylinder 514 may be connected to the outer cylinder 512 and extends into the cavity 526. The inner cylinder 514 may be connected to the outer cylinder 512 in a variety of ways known to those skilled in the art. For example, the inner cylinder 514 may be fused to the outer cylinder 512. Inner cylinder 514 may have grooves 532 therein adapted to accommodate a suture 524.

A tapered bone anchor receptacle 516 extends from the proximal end 534 of the inner cylinder 514. The tapered bone anchor receptacle 516 may extend from the proximal end 534 of the inner cylinder 514 by a distance of from about 0.3 inches to about 0.7 inches. Preferably, the tapered bone anchor receptacle 516 extends from the proximal end 534 of the inner cylinder 514 by a distance of from about 0.4 inches to about 0.6 inches. More preferably, the tapered bone anchor receptacle 516 extends from the proximal end 534 of the inner cylinder 514 by a distance of about 0.5 inches.

The proximal end 540 of the tapered bone anchor receptacle 516 preferably has a width smaller than that of the proximal end 534 of the inner cylinder 514. This configuration produces a shoulder 538 which may serve as a depth stop to ensure that the bone anchor 518 may be driven into the bone to the desired depth.

The proximal end 540 of the tapered bone anchor receptacle 516 may be from about 0.08 inches to about 0.12 inches in width. Preferably, the proximal end 540 of the tapered bone anchor receptacle 516 is from about 0.09 inches to about 0.110 inches in width. More preferably, the proximal end 540 of the tapered bone anchor receptacle 516 is 0.1 inches in width.

The distal end 536 of the tapered bone anchor receptacle 516 may be from about 0.110 inches to about 0.15 inches in width. Preferably, the distal end 536 of the tapered bone anchor receptacle 518 is from about 0.12 inches to about 0.14 inches in width. More preferably, the distal end 536 of the tapered bone anchor receptacle 516 is 0.13 inches in width. The distal end 536 of the tapered bone anchor receptacle 516 may have a variety of cross sectional shapes adapted to releasably engage the bone anchor 518. For example, the distal end 536 of the tapered bone anchor receptacle 516 may be square, rectangular, pentagonal, triangular or hexagonal in cross section.

The tapered bone anchor receptacle 516 may have a notch 542 therein in which the bone anchor 518 may be releasably seated. Alternatively, the outer cylinder, inner cylinder, and tapered bone anchor receptacle may be a single integral component.

The bone anchor implantation device may have a protective sheath 544 connected to the bone anchor-mount 510 which protects the point of the bone anchor from tissue contact during placement of the device and also protects the bone anchor from contacting potentially infectious microorganisms. The protective sheath 544 comprises a first telescoping cylinder 546 and a second telescoping cylinder 548. A spring 550 biases the first telescoping cylinder 546 and the second telescoping cylinder 548 to a position in which they extend from the outer cylinder 512 and cover the bone anchor 518. The first and second telescoping cylinders 546, 548 may be made of a variety of materials such as stainless steel or plastic. Preferably, the first and second telescoping cylinders 546, 548 are made of stainless steel.

The first telescoping cylinder 546 has a lumen 552 extending therethrough. The first telescoping 546 cylinder has a first shoulder 554 which engages shoulder 530 on the outer cylinder 512 and a second shoulder 556 which engages a first shoulder 558 on the second telescoping cylinder 548. The second telescoping cylinder 548 has a first shoulder 558 which engages the second shoulder 556 on the first telescoping cylinder 546 as described above. A second shoulder 560 may be located at the proximal end of the second telescoping cylinder 548 and engages the spring 550. The second telescoping cylinder 548 also has a lumen 562 extending there through which may be in fluid communication with the lumen 552 of the first telescoping cylinder 546 and the cavity 526 in the outer cylinder 512.

Figure 12A:
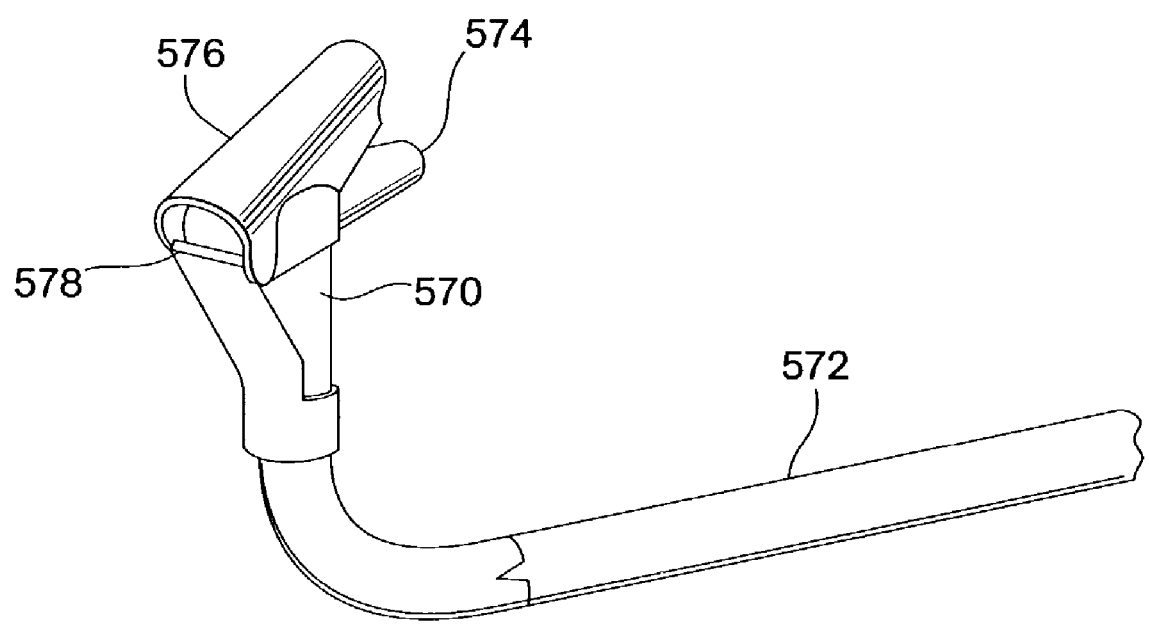
FIG. 12A is a perspective view of a bone anchor-mount protective sheath.
Figure 12B:
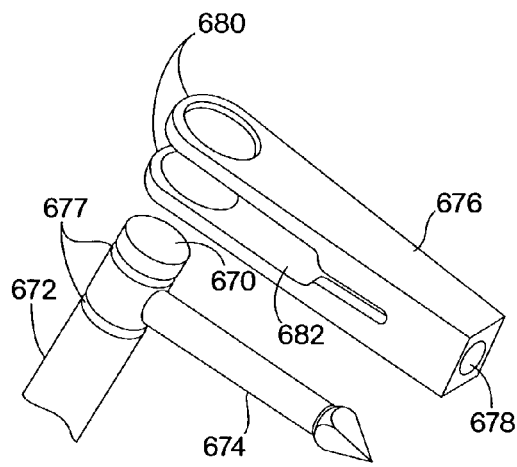
FIG. 12B is a perspective view of a protective sheath detached from a bone anchor mount.
Figure 12C:
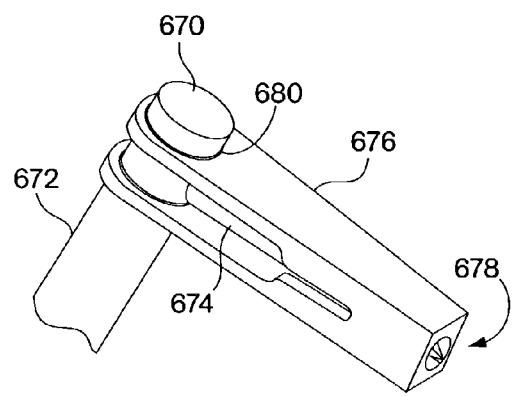
FIG. 12C is a perspective view of a protective sheath attached to a bone anchor mount in an extended position.
Figure 12D:
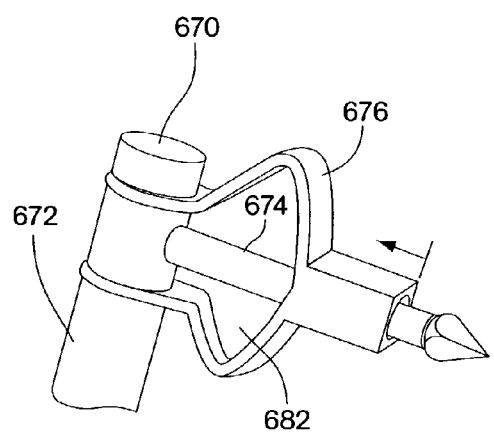
FIG. 12D is a perspective view of a protective sheath attached to a bone anchor mount in a compressed position, showing a protruding bone anchor.
Figure 12E:
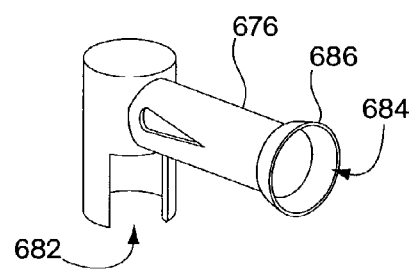
FIG. 12E is a perspective view of a protective sheath.

In the embodiments of the invention illustrated in FIGS. 12A–12E, the outer end 570, 670 of the shaft 572, 672 and the bone anchor-mount 574, 674 are covered by a flexible hood 576, 676. Referring to FIG. 12A, the flexible hood 576 may be removable, and may have a hinge region 578. In an alternative embodiment pictured in FIG. 12B, the flexible hood 676 snaps on to the outer end 670 of the shaft 672, e.g., facilitated by grooves 677 in the outer end 670 of the shaft 672 which receive edges defined by holes 680 in the hood 676. FIG. 12B shows an unattached hood 676 and a shaft 672. FIG. 12C shows the hood 676 attached to a shaft 672, with the hood 676 in an extended position covering the bone-anchor mount 674. FIG. 12D shows the hood configuration of FIG. 12C in its collapsed or compressed position, the flexible walls of the hood 676 bending outward allowing the bone anchor to protrude from the hood 676. In this embodiment, when a bone anchor is installed, the hood 676 collapses and slides back on the bone anchor mount 674 as illustrated in FIG. 12C. Another version of the hood of the invention is illustrated in FIG. 12E. In this version, the hood comprises a chamber 682 shaped to fit the outer end 670 of the shaft 672. In that embodiment, the hood 676 comprises a flaired region 684 at the distal end of the hood 686. The hood compresses in a manner analogous to that shown in FIG. 12D when the bone anchor is being placed. In a preferred embodiment, the material used to make the hoods is a soft or pliable material, such as soft rubber or silicone.

Figure 13:
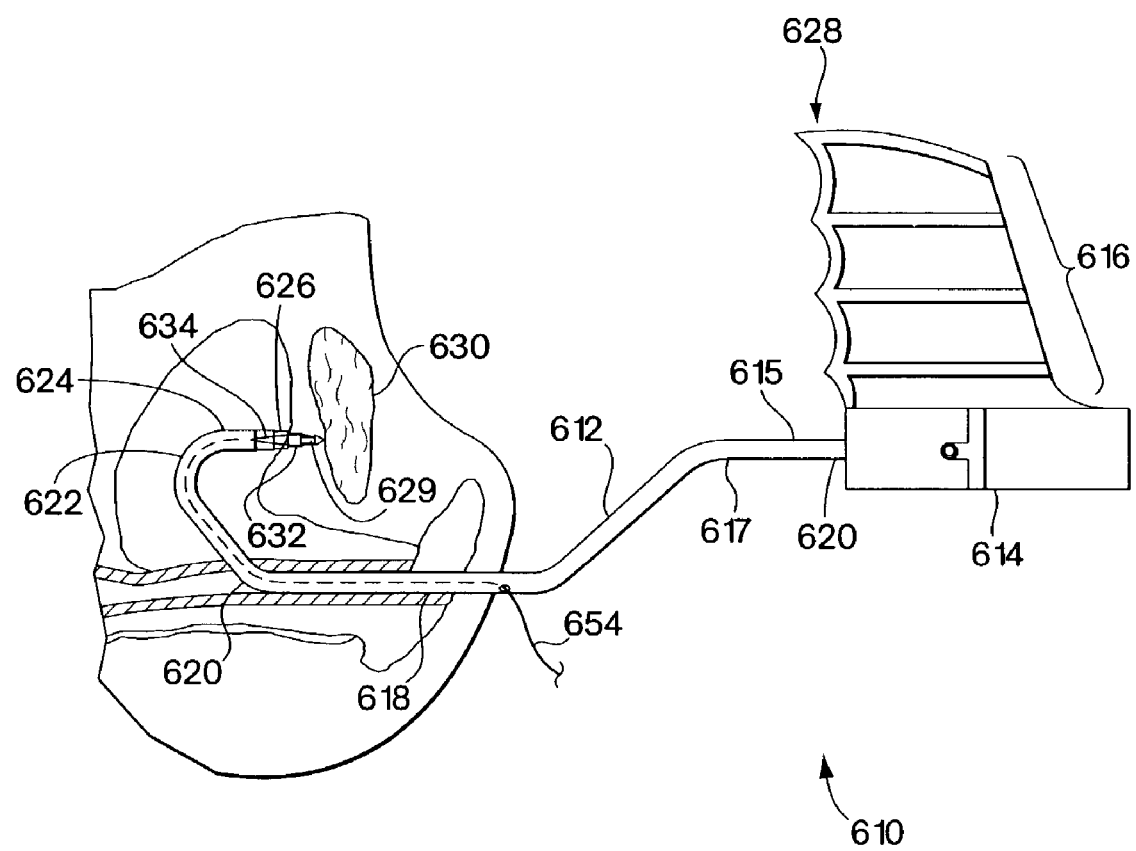
FIG. 13 is a schematic view showing the bone anchor implantation device inserted into the vagina with the proximal end of the second telescoping cylinder contacting the pubic bone.

An alternative embodiment of the bone anchor implantation device 610 is shown in FIG. 13. As illustrated therein, the shaft 612 has a generally straight proximal section 615, a first generally bent section 617, a generally straight median section 618, a second bent section 620, a generally curved section 622, and a distal generally straight section 624. The first bent section 617 may bend at an angle of from about 35° to about 55° relative to the straight proximal section 615. Preferably, the first bent section 617 bends at an angle of from about 40° to about 50° relative to the straight proximal section 615. More preferably, the first bent section 617 bends at an angle of about 45° relative to the straight proximal section 615.

The second bent section 620 may bend at an angle of from about 125° to about 145° relative to the straight median section 618. Preferably, the second bent section 620 bends at an angle of from about 130° to about 140° relative to the straight median section 618. More preferably, the second bent section 620 bends at an angle of about 135° relative to the straight median section 618.

The curved section 622 may curve through an arc of from about 70° to about 110° with a radius from about 0.2 inches to about 0.6 inches. Preferably, the curved section curves 622 through an arc of from about 80° to about 100° with a radius from about 0.3 inches to about 0.5 inches. More preferably, the curved section 622 curves through an arc of about 90° with a radius of 0.4 inches.

Figure 15:
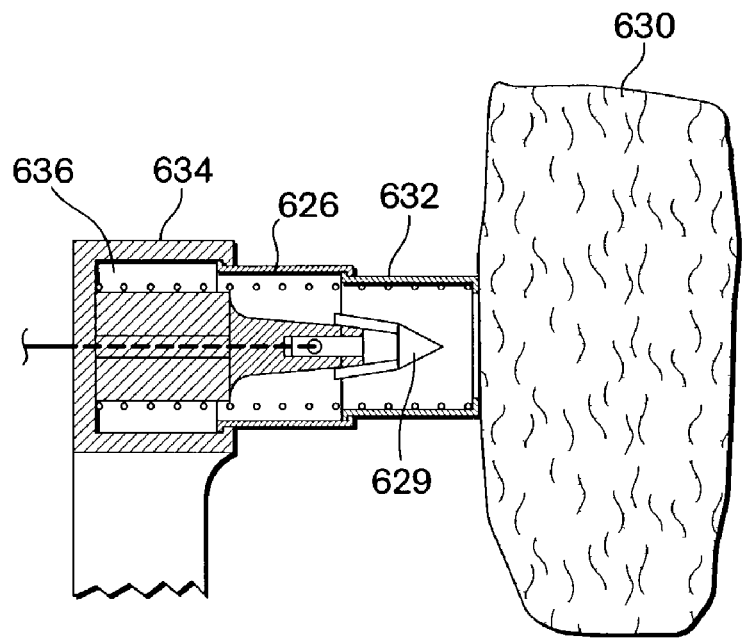
FIG. 15 is a cross sectional view of the bone anchor-mount and protective sheath when the protective sheath is contacting the pubic bone.
Figure 16:
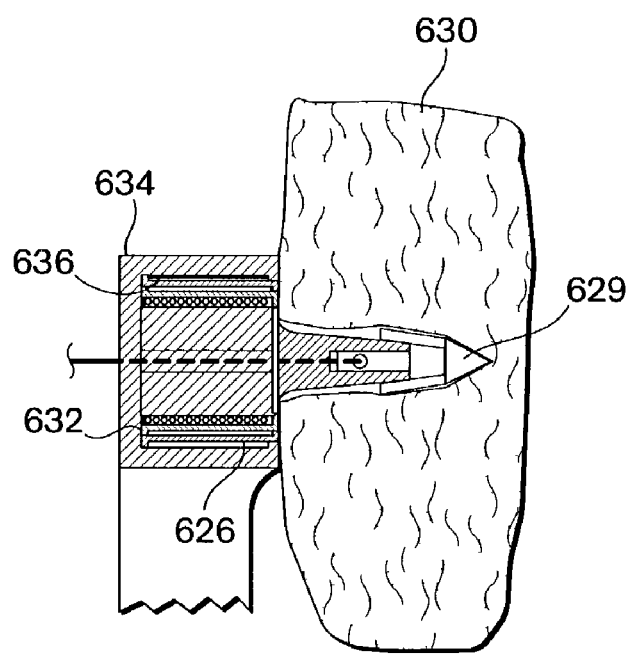
FIG. 16 is a cross sectional view of the bone anchor-mount and the protective sheath when the bone anchor is being implanted into the pubic bone.

The bone anchor implantation device 610 may be inserted transvaginally as shown in FIG. 13 with the patient in the lithotomy position and the surgeon located between the patient's legs. As used herein, the terms "transvaginally" or "transvaginal access" refer to access through the vaginal introitus or from within the vagina. An incision in the anterior vaginal wall may be made. The shaft 612 may be inserted through the incision and the protective sheath may be positioned such that the proximal end of the second telescoping cylinder 632 contacts the pubic bone 630. At this time, the first and second telescoping cylinders 626, 632 are biased to a position in which they extend from the outer cylinder 634 to cover the bone anchor 629. The bone anchor 629 may be inserted into the bone by applying a retrograde force to the bone anchor 629. For example, the handle may be pulled in a retrograde direction (toward the user) to implant the anchor. As best illustrated in FIGS. 15 and 16, as the device is pulled in a retrograde motion, the first and second telescoping cylinders 626, 632 retract inside the cavity 636 of the outer cylinder and the bone anchor 629 may be driven into the pubic bone 630. Because the patient's body weight provides an opposing force, the user need only apply a small amount of force, such as 10–20 pounds, in order to drive the bone anchor 629 into the bone 630. The device 610 may then be pushed away from the implanted anchor to disengage the device from the anchor. The device may then be removed from the vagina, leaving the bone anchor 629 in the bone 630 with the suture extending therefrom. The bladder neck may then be compressed, suspended or stabilized using the suture(s) extending from the bone anchor(s) as described above.

Figure 14:
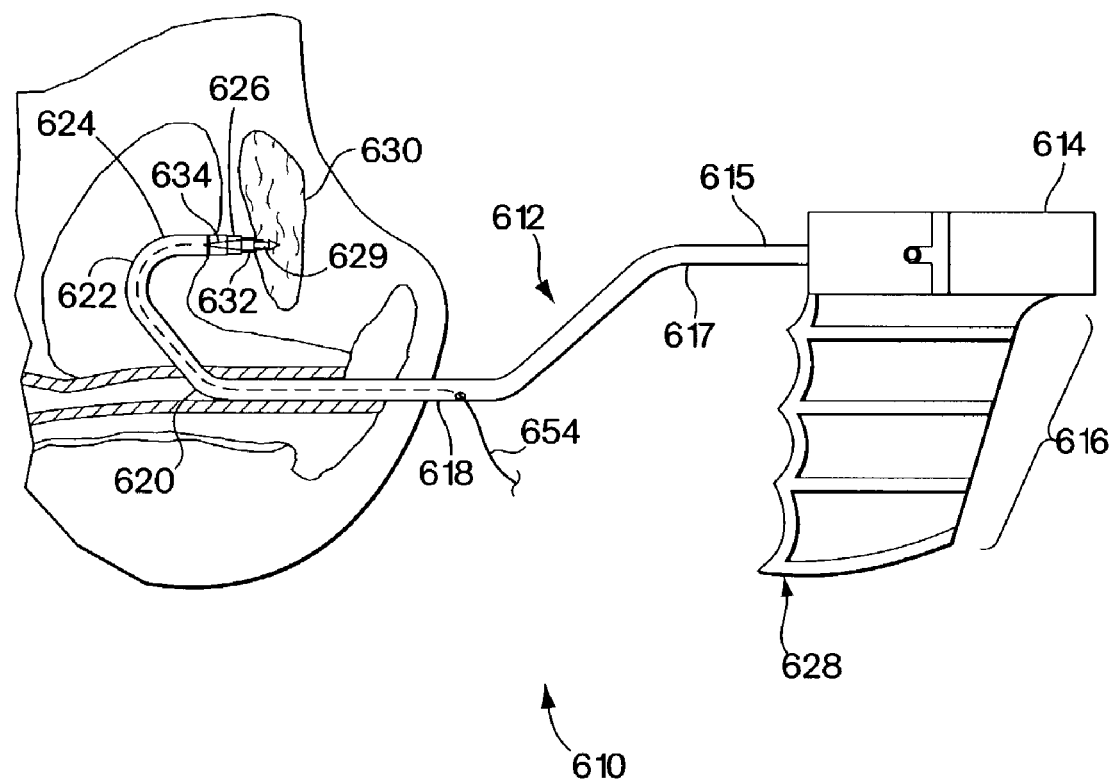
FIG. 14 is a schematic view showing an embodiment of the bone anchor implantation device illustrated in FIG. 13 wherein the handle has been rotated after insertion into the vagina, and showing the implantation of a bone anchor into the pubic bone and the compression of the spring.

In another version of the method, the handle 616 may be rotated after insertion into the vagina and prior to providing the retrograde force for implanting the bone anchor. FIG. 13 illustrates a bone anchor delivery device in a first position. By compressing the handle 616 and rotating the handle 616 relative to the shaft 612 as described previously herein, the handle 616 can be moved to a second position, e.g., as illustrated in FIG. 14. Once in the second position, a retrograde force can be applied to insert the bone anchor 629 into the bone 630.

The methods and devices of the present invention drive a bone anchor through, for example, the vaginal wall and into the posterior portion of the pubic bone or symphysis pubis. At least one bone anchor may be driven into the pubic bone on either side of the urethra. However, one of skill in the art will appreciate that a single bone anchor may also be used. At least one suture may be attached to the bone anchors which may extend through the vaginal wall and may then be attached to the endopelvic fascia, the vaginal wall, a sling, or other material to stabilize and/or slightly compress the urethra, thereby improving or maintaining the patient's urinary continence.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims.

I claim:

1. A device for manually implanting a bone anchor into a bone, comprising:
    a handle including a proximal end and a distal end, the distal end comprising a distally facing surface having at least two distally facing finger indentations;
    a shaft including a first end and a second end, said first end being connected to and extending from said distal end of said handle at a location between said at least two distally facing finger indentations; and
    a bone anchor-mount for releasably engaging said bone anchor, said bone anchor-mount being connected to said second end of said shaft and pointed at said at least two distally facing finger indentations so that said bone anchor may be implanted into the bone by manually applying a retrograde force to said handle.

2. A method for manually implanting a bone anchor into a bone, comprising the steps of:
    inserting into a body cavity a device comprising a handle including a proximal end and a distal end, the distal end comprising a distally facing surface having at least two distally facing finger indentations; a shaft including a first end and a second end, said first end being connected to and extending from said distal end of said handle at a location between two of said distally facing finger indentations; and a bone anchor-mount pointed at said at least two distally facing finger indentations for releasably engaging said bone anchor,
    locating an implantation site for the bone anchor; and
    applying a retrograde force to said handle, thereby implanting the bone anchor and
    releasing the bone anchor from the device.

\* \* \* \* \*